(12) United States Patent
Ko et al.

(10) Patent No.: US 8,383,602 B2
(45) Date of Patent: Feb. 26, 2013

(54) USE OF TRIM72 AS A TARGET FOR MUSCLE AND HEART ENHANCER

(75) Inventors: Young-Gyu Ko, Seoul (KR); Jae-Sung Yi, Seoul (KR); Chang-Seok Lee, Seoul (KR)

(73) Assignee: Korea University Industrial & Academic Collaborative Foundation, Seoul (KR)

( * ) Notice: Subject to any disclaimer, the term of this patent is extended or adjusted under 35 U.S.C. 154(b) by 92 days.

(21) Appl. No.: 12/733,484

(22) PCT Filed: Sep. 4, 2008

(86) PCT No.: PCT/KR2008/005234
§ 371 (c)(1),
(2), (4) Date: Mar. 4, 2010

(87) PCT Pub. No.: WO2009/031842
PCT Pub. Date: Mar. 12, 2009

(65) Prior Publication Data
US 2011/0251256 A1     Oct. 13, 2011

Related U.S. Application Data

(60) Provisional application No. 60/969,941, filed on Sep. 4, 2007.

(51) Int. Cl.
*A61P 9/00*     (2006.01)
*A61K 31/70*    (2006.01)
*C12Q 1/68*     (2006.01)

(52) U.S. Cl. ...... 514/44 A; 514/1.1; 514/44 R; 435/375; 435/377

(58) Field of Classification Search .................. None
See application file for complete search history.

(56) References Cited

FOREIGN PATENT DOCUMENTS
WO     2008-054561 A2     5/2008

OTHER PUBLICATIONS

Brummelkamp, T.R. et al., "A System for Stable Expression of Short Interfering RNAs in Mammalian Cells," Science, vol. 296, pp. 550-553 (Apr. 19, 2002).
Elbashir, S. M. et al., "RNA interference is mediated by 21- and 22-nucleotide RNAs," Genes & Development, 15:188-200 (2001).
Fire, A. et al., "Potent and specific genetic interference by double-stranded RNA in *Caenorhabditis elegans*," Nature, vol. 391, pp. 806-811 (Feb. 19, 1998).
Kudryashova, E. et al., "Trim32 is a Ubiquitin Ligase Mutated in Limb Girdle Muscular Dystrophy Type 2H that Binds to Skeletal Muscle Myosin and Ubiquitinates Actin," J. Mol. Biol., 354, pp. 413-424 (2005).
Lee, N.S. et al., "Expression of small interfering RNAs targeted against HIV-1 rev transcripts in human cells," Nature Biotechnology, vol. 19, pp. 500-505 (May 2002).
Martinez, J. et al., "Single-Stranded Antisense SiRNAs Guide Target RNA Cleavage in RNAi," Cell, vol. 110, pp. 563-574 (Sep. 6, 2002).
Miyagishi, M. et al., "U6 promoter-driven siRNAs with four uridine 3 foot overhangs efficiently suppress targeted gene expression in mammalian cells," Nature Biotechnology, vol. 19, pp. 497-500 (May 2002).
Paddison, P.J. et al., "Short hairpin RNAs (shRNAs) induce sequence-specific silencing in mammalian cells," Genes & Development, 16:948-958 (2002).
Strausberg, R. L. et al., "Mus musculus tripartite motif-containing 72 (Trim72), mRNA," NCBI genbank No. (NM_001079932) (Jun. 2007).
Tuschl, T.. "Expanding small RNA interference," Nature Biotechnology, vol. 20, pp. 446-448 (May 2002).
Tuschl, T. et al., "Selection of siRNA duplexes from the target mRNA sequence," http://www.rockefeller.edu/labheads/tuschl/sima.html, May 6, 2004.
European Search Report for European Application No. 08829316.2, dated Jun. 9, 2011.

*Primary Examiner* — Sean McGarry
(74) *Attorney, Agent, or Firm* — Edwards Wildman Palmer LLP

(57) ABSTRACT

The present invention relates to a new use of TRIM72 as a target for muscle enhancer and heart enhancer, more particularly to a composition for enhancing muscle or heart comprising an expression or action inhibitor of TRIM72 protein. The present invention further relates to a new TRIM mutant protein inducing muscle differentiation and hypertrophy and its gene. The inventors of the present invention have identified that TRIM72 overexpression inhibits myogenesis whereas TRIM72 knockdown enhances myogenesis, and first elucidated that TRIM72 is a negative regulator of skeletal muscle differentiation. Accordingly, the inhibition of TRIM72 acts exclusively on skeletal muscle and heart muscle, but does not affect IGF-I signaling pathway in other tissues. Therefore, a drug or gene therapy using TRIM72 as a target may be helpful in treating obesity and type 2 diabetes by promoting skeletal muscle differentiation, hypertrophy and energy consumption in adipose tissue and inducing strong muscle by promoting physiological hypertrophy of heart muscle, without cancer or other side effects.

15 Claims, 26 Drawing Sheets
(16 of 26 Drawing Sheet(s) Filed in Color)

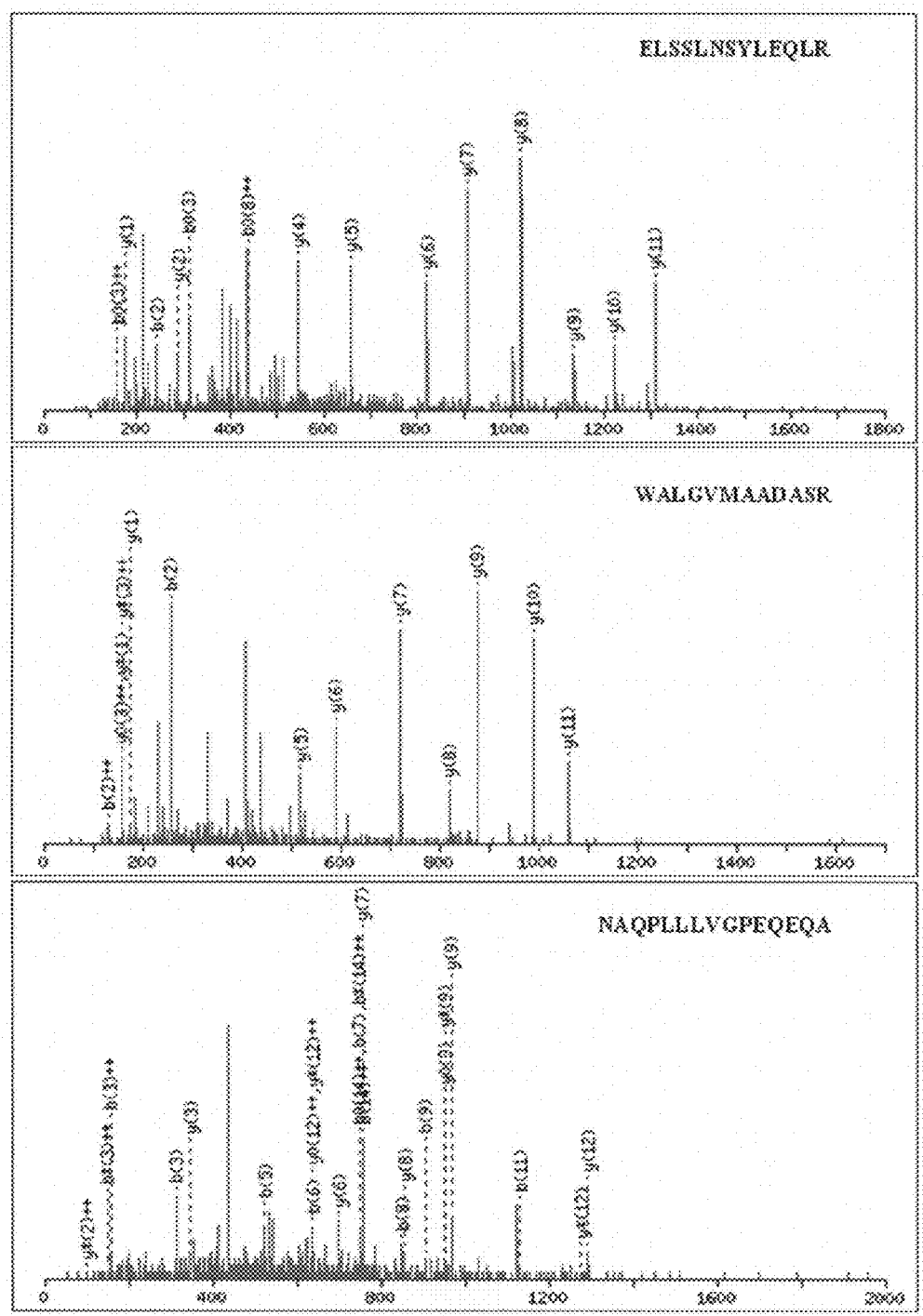
FIG. 3A-continued

FIG. 3B

MSAAPGLLRQELSCPLCLQLFDAPVTAECGHSFCRACLIRVAGEPAADGTVACPCCQAPTRPQ
ALSTNLQLSRLVEGLAQVPQGHCEEHLDPLSIYCEQDRTLVCGVCASLGSHRGHRLLPAAEAQ
ARLKTQLPQQKMQLQEACMRKEKTVAVLEHQLVEVEETVRQFRGAVGEQLGKMRSIFLAAL
ESSLDREAERVRGDAGVALRRELSSLNSYLEQLRQMEKVLEEVADKPQTEFLMKFCLVTSRL
QKILSESPPPARLDIQLPVISDDFKFQVWKKMFRALMPALEELTFDPSSAHPSLVVSSSGRRV
ECSDQKAPPAGEDTRQFDKAVAVVAQQLLSQGEHYWEVEVGDKPRWALGVMAADASRRG
RLHAVPSQGLWLLGLRDGKILEAHVEAKEPRALRTPERPPARIGLYLSFADGVLAFYDASNPD
VLTPIFSFHERLPGPVYPIFDVCWHDKGKNAQPLLLVGPEQEQA

FIG. 3C

Ring  B-box Coiled-coil  SPRY

WCL, whole cell lysate
Cyto, cytoplasme
PM, plasma membrane

Consensus Sequence of Ring Finger Domain, $Zn^{2+}$ binding site
CX2CX(9-39)CX(1-3)HX(2-3)C/HX2CX(4-48)CX2C <u>TRIM72 sequence</u>
MSAAPGLLHQELSCPLCLQLFDAPVTAECGHSFCRACLGRVAGEPAADGTVLCPCCQAPT
RPQALSTNLQLARLVEGLAQVPQQHCEEHLDPLSIYCEQDRALVCGVCASLGSHRGHRLLP
AAEAHARLKTQLPQQKLQLQEACMRKEKSVAVLEHQLVVEETVRQFRQAVGEQLGKMR
VFLAALEGSLDCEAERVRGEAGVALRRELGSLNSYLEQLRQMEKVLEEVADKPQTEFLMK
YCLVTSRLQKILAESPPPARLDIQLPIISDDFKFQVWRKMFRALMPALEELTFDPSSAHPSLV
VSSSGRRVECSEQKAPPAGEDPRQFDKAVAVVAHQQLSEGEHYWEVDVGDKPRWALGVI
AAEAPRRGRLHAVPSQGLWLLGLREGKILEAHVEAKEPRALRSPERRPTRIGLYLSFGDGV
LSFYDASDADALVPLFAFHERLPRPVYPFFDVCWHDKGKNAQPLLLVGPEGAEA

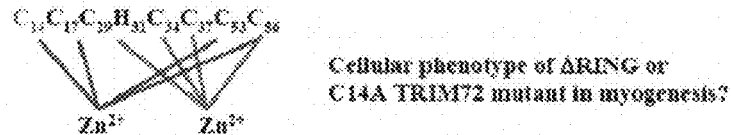

Cellular phenotype of ΔRING or
C14A TRIM72 mutant in myogenesis?

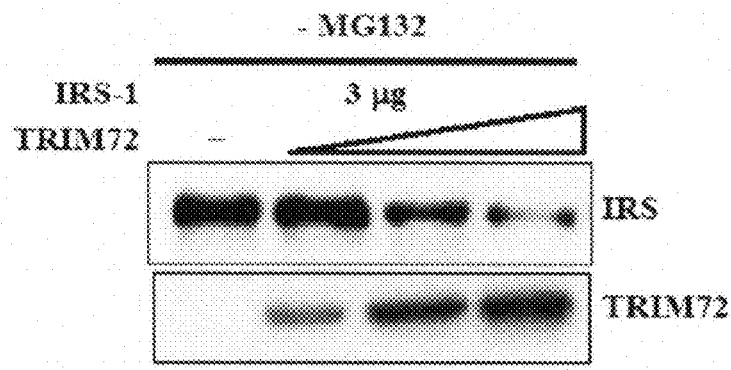

ChIP assay

USE OF TRIM72 AS A TARGET FOR MUSCLE AND HEART ENHANCER

TECHNICAL FIELD

The present invention relates to a new use of TRIM72 as a target for muscle enhancer and heart enhancer, more particularly to a composition for enhancing muscle or heart comprising an expression or action inhibitor of TRIM72 protein. The present invention further relates to a new TRIM mutant protein inducing muscle differentiation and hypertrophy and its gene.

BACKGROUND ART

Although knowledge about molecular mechanism of cell differentiation and tissue formation is accumulating very quickly, it is still unclear how the size of an organ is regulated. 40 years ago, Bullough proposed a hypothesis that a negative growth regulator called the "chalone (an endocrine substance inhibits the physiological action)" regulates the size of an organ [Bullough W S., *Cancer Res.*, 25, 1683, 1965]. According to the hypothesis, when an organ grows to a certain size, it secretes the chalone so that it cannot grow further. The chalone was not discovered in spite of extensive researches over the last 40 years, and the hypothesis seemed to be abandoned. But, recently, a chalone called myostatin was found in skeletal muscle.

Myostatin (myo means muscle, and statin means stop), a member of the transforming growth factor-β superfamily, is expressed in skeletal muscle. A significantly increased skeletal muscle mass was found in myostatin-deficient mouse [McPherron A C. et al., *Nature*, 387, 83, 1997]. Myostatin mutation was found in not only in double-muscled Belgian Blue and Pidemontese cattle [McPherron A C. et al., *PNAS*, 94, 12457, 1997], but also in with gross muscle hypertrophy [Schuelke, M. et al., *New Eng. J. Med.*, 350, 2682, 2004]. These findings prove that myostatin is the chalone that regulates the size of muscle. In myostatin −/− mice, the muscle mass increases while the accumulation of fats decreases remarkably. When obese (ob/ob) mice were bred with myostatin −/− mice, the offspring exhibited normal body weight, reduced fats and normal blood sugar level [McPherron A C. and Lee, S J., *J. Clin. Invest.*, 109, 595, 2002]. This indicates that obesity and type 2 diabetes may be treated by reducing the amount of myostatin or inhibiting its activity. In addition, it was shown that when mice with muscular dystrophy induced by dystrophin deficiency were treated with anti-myostatin antibody, muscle length and diameter were restored as those of normal mice [Bongdanovich S., *Nature*, 420, 416, 2002]. This implies that anti-myostatin antibody may be used for the treatment of muscular dystrophy patients. Actually, Wyeth (USA) is carrying out clinical trials on myostatin. However, because myostatin-deficient mice and myostatin mutant cattle lose their reproductive ability [*Animal Genetics*, 36, 1, 2004; *J. Gene Med.*, 8, 1171, 2006, drugs using myostatin as a target may result in severe adverse reactions.

Whereas myostatin regulates muscle size negatively, insulin-like growth factor (IGF-I) regulates it positively. For example, mice in which IGF-I was overexpressed only in muscle using muscle-specific promoter exhibited two times more muscle mass than normal mice [Masaro A. et al., *Nature Genet.*, 28, 195, 2001]. Thus, there was a medical attempt to use IGF-I as muscle enhancer. But, this attempt met serious obstacles. For one thing, because IGF receptors are expressed in nearly every cell, the administration of IGF-I may have a serious effect not only on muscle but also on other tissues. Besides, IGF-I promotes cell division and proliferation, thereby resulting in unwanted hyperproliferation of tissues. Accordingly, it is needed to induce selective expression of IGF-I only in muscle (through genetic treatment) or selective IGF-I signaling only in muscle.

FIG. 1 schematically illustrates the IGF-I signaling. When the signaling pathway IRS-1→PI3K→AKT-1→mTOR→p70$^{S6K}$ which is activated by IGF-I is blocked (using mice with deficiency of each gene), the mice become smaller in size and the muscle mass decreases abruptly. And, in PTEN- and SHIP$_2$-deficient mice, the amount of Ptd Ins(3, 4,5)P$_3$ increases to induce overexpression of PI3K/AKT1. As a result, the muscle mass increases [Glass, D J., *Nat. Cell Biol.*, 5, 87, 2003]. These results show that PI3K, AKT-1, mTOR, p70$^{S6K}$ and GSK3β might be good candidate target proteins for the development of muscle enhancer. However, because these proteins affect not only muscle but also other tissues, activation (PI3K, AKT-1, mTOR, p70$^{S6K}$ or GSK3β) or inhibition (PTEN or SHIP$_2$) using the proteins may lead to adverse reactions such as cancer. Accordingly, these proteins are not good targets for the development of muscle enhancer.

The inventors of the present invention isolated lipid rafts from C2C12 myoblasts and myotubes, and identified TRIM72, the function of which was never known yet, through comparative proteomics. TRIM72 has a (ubiquitin E3) TRIM/RBCC domain necessary for ubiquitin E3 ligase activity. TRIM72 is specifically expressed in lipid rafts of skeletal muscle and heart and results in increased muscle mass during muscle differentiation. Overexpression of TRIM72 inhibits myogenesis, whereas knockdown of TRIM72 enhances myogenesis. This signifies that TRIM72 is a negative regulator of skeletal muscle differentiation. TRIM72 regulates the IGF-I/IGFR/IRS-1 signaling pathway by inhibiting IGF-1-mediated activation of IRS-1 through interaction with IRS-1. Accordingly, TRIM72 acts only on skeletal muscle and heart, without affecting the IGF-I signaling pathway in other tissue. Therefore, cancer or other side reactions may be prevented. That is, a drug or genetic treatment using TRIM72 as target may lead to the treatment of obesity and type 2 diabetes without side effects, by promoting differentiation and hypertrophy of skeletal muscle and energy consumption in adipose tissue, and to a strong heart, by promoting physiological hypertrophy of heart muscle.

[Disclosure]
[Technical Problem]

In an aspect, there is provided a new use of TRIM72 as a target for muscle and heart enhancer.

In another aspect, there is provided a composition for enhancing muscle or heart comprising an expression or action inhibitor of the TRIM72 protein.

In another aspect, there is provided a method for enhancing muscle or heart, which comprises administering an expression or action inhibitor of the TRIM72 protein.

In another aspect, there is provided a new TRIM mutant protein or its gene having activity of promoting muscle differentiation and hypertrophy.

[Technical Solution]

According to an embodiment of the present invention, there is provided a composition for enhancing muscle or heart comprising an expression or action inhibitor of TRIM72 protein as an effective ingredient. It is first proposed in the present invention that inhibition of expression or action of TRIM72, a negative regulator of muscle differentiation, promotes muscle differentiation and hypertrophy and may lead to enhancement of muscle or heart.

TRIM72 is an abbreviation of tripartite motif-containing 72 and has a RING domain, a B box, a coiled-coil domain and a SPRY domain, as shown in FIG. 3C. Base sequence and amino acid sequence of mouse TRIM72 may be obtained from NCBI Accession No. NM_001079932. The amino acid sequence of mouse TRIM72 protein is given as SEQ ID NO: 1. Base sequence and amino acid sequence of human TRIM72 may be obtained from NCBI Accession No. NM_001008274. The amino acid sequence of human TRIM72 protein is given as SEQ ID NO: 2. The mouse and human TRIM72 are expected to have the same function, because their amino acid sequences have 90% identity. But, their function was not elucidated as yet.

For the expression or action inhibitor of TRIM72 protein, any substance known to inhibit expression or action of protein may be used. Preferably, a composition for enhancing muscle or heart which downregulates transcription or translation of TRIM72 gene or inhibits action of TRIM72 protein is provided. As used herein, "downregulation of transcription or translation of TRIM72 gene" includes downregulation of transcription by binding to the TRIM72 promoter gene, degradation of mRNA after transcription, interruption of translation, or any other downregulation. And, "inhibition of action of TRIM72 protein" includes inhibition of protein activity and interruption of protein interaction with other proteins by competitively binding.

Examples of the expression inhibitor of TRIM72 protein may include siRNA (short interfering RNA) using RNA interference of TRIM72 gene or shRNA (short hairpin RNA). RNA interference (hereinafter, "RNAi") is a mechanism that inhibits gene expression after transcription in many eukaryotes. RNAi is induced by short double-stranded RNA ("dsRNA") molecules existing in cells [Fire A. et al., (1998), Nature 391: 806-811]. These short dsRNA molecules also known as the "siRNA" are separated into single strands and bind to "RNA-induced silencing complex (RISC)", thereby cleaving target mRNA or interfering translation [Elbashir S M et al., (2001), Genes Dev., 15: 188-200].

Thus, the present invention provides a separated siRNA comprising short double-stranded RNA consisting of from about 17 to about 25 nucleotides targeting mRNA of TRIM72 gene. The siRNA comprises a sense RNA strand and its complementary antisense RNA strand. These two strands bind (anneal) with each other through Watson-Crick base pairing interaction. The sense strand includes the same nucleotide sequence in the target sequence of the target mRNA. The target sequence of siRNA may be selected by a method published in the literature, e.g., [Tuschl T. et al., "The siRNA User Guide" revised Oct. 11, 2002]. The TRIM72 target sequence used to manufacture the siRNA of the present invention is 5'-AAGCACGCCUCAAGACACAG-3'.

The sense and antisense strands of the siRNA of the present invention may include two complementary, single-stranded RNA molecules, or a molecule wherein two complementary moieties are base-paired and covalently bonded by a single-stranded "hairpin" domain. The latter is called shRNA (short hairpin RNA). shRNA is a single strand, about 50-70 nucleotides in length, having a stem-loop structure in vivo. On both sides of 5-10 nucleotide loop portion, long RNA of 19-29 nucleotides are base-paired to form a double-stranded stem. In general, shRNA is synthesized in vivo from the Pol III promoter by the transcription of complementary DNA sequence. The Pol-III-induced transcription starts from the well-defined start site and terminates at the linear second residue consisting of 4 or more thymidines (-TTTT-) to form a non-poly(A) transcript. The Pol III promoter is activated in all cells and can express the shRNA. Following the transcription, the shRNA has its loop cleaved by Dicer, and interacts with RISC like siRNA [see Tuschl, T. (2002), Cell 110(5): 563-74].

The siRNA of the present invention may be obtained by the method well known to those skilled in the related art. For example, the siRNA may be synthesized chemically or produced by recombinant technique using the method well known in the related art. Preferably, the siRNA of the present invention may be synthesized chemically using adequately protected ribonucleoside phosphoramidites and a commonly used DNA/RNA synthesizer. The siRNA may be synthesized as two separated complementary RNA molecules or as an RNA molecule having two complementary domains. Alternatively, the siRNA may be expressed from a recombinant DNA plasmid using an adequate promoter. Examples of the adequate promoter for expressing the siRNA of the present invention from plasmid may include U6 or H1 RNA pol III promoter and cytomegalovirus promoter. Further, the recombinant plasmid may include an inducing promoter or a controllable promoter so that the siRNA can be expressed under a specific tissue or cell environment.

The siRNA of the present invention may be expressed from the recombinant plasmid as two separated complementary RNA molecules or as an RNA molecule having two complementary domains. Selection of adequate plasmid for expressing the siRNA of the present invention, insertion of nucleotide sequence for expressing the siRNA into the plasmid, and transfer of the recombinant plasmid to target cells are disclosed in the related art. For example, refer to the literatures [Tuschl, T. (2002), Nat. Biotechnol., 20: 446-448; Brummelkamp T R et al. (2002), Science 296: 550-553; Miyagishi M. et al., (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508], which are incorporated herein by reference.

In the composition for enhancing muscle or heart of the present invention, the expression inhibitor of TRIM72 protein may be TRIM72 siRNA (short interfering RNA) having a base sequence complementary to mRNA of TMRIM72 gene, more preferably a base sequence of SEQ ID NO: 3, or a gene which transcribes the same.

In the composition for enhancing muscle or heart of the present invention, the action inhibitor of TRIM72 protein may be a substance that interferes with the interaction of TRIM72 with IRS-1 or M-Cadherin. As it was found out that the coiled-coil domain of TRIM72 binds with the Mid and Rear regions of IRS-1 (see FIG. 9), a peptide which binds specifically to the binding domain and can competitively inhibit the interaction may be designed. Further, polyclonal or monoclonal antibody against TRIM72 may be used as the interaction inhibitor.

The polyclonal antibody may be prepared by injecting the immunogen TRIM72 protein or its fragment into a host by the method well known to those skilled in the art. The host may include a mammal such as mouse, rat, sheep and rabbit. The immunogen may be injected intramuscularly, intra-abdominally or subcutaneously. An adjuvant may be administered together in order to enhance antigenicity. Blood is taken from the host at predetermined intervals to collect the serum showing improved titer or antigen specificity, or antibody is isolated and purified therefrom.

The monoclonal antibody may be prepared by fusing with an immortalized cell line as well known in the related art [Koehler and Milstein (1975) Nature, 256:495]. The procedure is as follows. First, 20 μg of pure TRIM72 protein is obtained and Balb/C mouse is immunized using the same, or a peptide is synthesized and bound to bovine serum albumin and the mouse is immunized using the same. Then, antigen-producing lymphocyte isolated from the mouse is fused with human or mouse myeloma to produce immortalized hybridoma, or only the hybridoma cells producing monoclonal antibody are selected and proliferated by ELISA, and monoclonal antibody is isolated and purified from therefrom.

In the composition for enhancing muscle or heart of the present invention, the expression or action inhibitor of TRIM72 protein may enhance IGF-1-induced PI3K/AKT activation. The function of the inhibitor is demonstrated in Result 4.

The present invention further provides a composition for inhibiting muscle differentiation wherein tyrosine phosphorylation of IRS-1 is enhanced by the expression or action inhibitor of TRIM72 protein so as to improve interaction between IRS-1 and PI3K. The function of the inhibitor is demonstrated in Result 5.

In the composition for inhibiting muscle differentiation of the present invention, the expression or action inhibitor of TRIM72 protein may inhibit ubiquitination of IRS-1 or M-Cadherin induced by TRIM 72. The function of the inhibitor is demonstrated in Results 7 and 8.

In another embodiment, the present invention provides a method for screening muscle or heart enhancer comprising: (a) treating an agent in animal cells expressing TRIM72 protein; and (b) determining whether the expression of TRIM72 protein decreases as compared to a control group in which the animal cells are not treated with the agent. In the step (a), the animal cells may be intentionally transfected with a plasmid overexpressing TRIM72. In the step (b), the decrease of expression may be measured by RT-PCR in RNA level, or by Western blotting, etc. in protein level.

In another embodiment, the present invention provides a method for screening muscle or heart enhancer comprising: (a) treating an agent in animal cells expressing TRIM72 protein; and (b) determining whether the interaction of TRIM72 with IRS-1 or M-Cadherin is inhibited in the animal cells. In the step (a), the animal cells may be intentionally transfected with a plasmid overexpressing TRIM72. In the step (b), the inhibition of interaction may be measured by immunoprecipitation, GST pull-down assay, or the like.

In another embodiment, the present invention provides a composition for inhibiting muscle differentiation comprising a TRIM72 protein having an amino acid sequence of SEQ ID NO: 1 or 2 or a gene encoding for the same. It is first elucidated in the present invention that TRIM72 is a negative regulator of muscle differentiation and proposed that it can inhibit muscle differentiation by blocking IGF-1 signaling necessary for the muscle differentiation.

In the composition for inhibiting muscle differentiation of the present invention, the gene may be inserted in an animal cell expressing vector, more preferably in an adenoviral vector. For the plasmid vector, pCMV-Flag or pHM6-HA vector may be used. And, for the adenoviral vector, pAd/CMV/V5-DEST (Invitrogen) may be used.

In the composition for inhibiting muscle differentiation of the present invention, the TRIM72 protein may inhibit IGF-1-induced PI3K/AKT activation. The function of the TRIM72 protein is demonstrated in Result 4.

In the composition for inhibiting muscle differentiation of the present invention, the TRIM72 protein may bind to IRS-1 and reduce tyrosine phosphorylation of IRS-1, thereby inhibiting the interaction of IRS-1 with PI3K. The function of the TRIM72 protein is demonstrated in Result 5.

In the composition for inhibiting muscle differentiation of the present invention, the TRIM72 protein may promote ubiquitination of IRS-1 or M-Cadherin by interacting with them. The function of the TRIM72 protein is demonstrated in Results 7 and 8.

In another embodiment, the present invention provides an siRNA (short interfering RNA) molecule for TRIM72 gene having a base sequence of SEQ ID NO: 3. The siRNA targets 5'-AAGCACGCCUCAAGACACAG-3' of TRIM72 mRNA and has a sequence complementary to it.

In another embodiment, the present invention provides a TRIM72 mutant protein (ΔRING TRIM72) in which the RING domain is deleted from an amino acid sequence of SEQ ID NO: 1 or 2. SEQ ID NO: 1 is the amino acid sequence of mouse TRIM72. Of its RING domain (1st through 60th amino acids), all or part may be deleted. SEQ ID NO: 2 is the amino acid sequence of human TRIM72. Of its RING domain (1st through 60th amino acids), all or part may be deleted.

The present invention further provides a TRIM72 mutant protein having an amino acid sequence of SEQ ID NO: 4 or 5. SEQ ID NO: 4 is the amino acid sequence of mouse ΔRING TRIM72, and SEQ ID NO: 5 is the amino acid sequence of human ΔRING TRIM72.

In another embodiment, the present invention provides a TRIM72 mutant gene which has a base sequence encoding for the TRIM72 mutant protein (ΔRING TRIM72). The base sequence may be easily designed by deleting only the RING domain coding sequence from the base sequence of mouse or human TRIM 72 gene.

In another embodiment, the present invention provides a TRIM72 mutant protein (DN-TRIM72) in which the 14th amino acid in an amino acid sequence of SEQ ID NO: 1 or 2 is substituted from cystine to alanine.

In another embodiment, the present invention provides a TRIM72 mutant gene which has a base sequence encoding for the RIM72 mutant protein (DN-TRIM72). The base sequence may be easily designed by substituting the 14th codon in a base sequence of a mouse or human TRIM 72 gene from a cystine codon to an alanine codon.

In another embodiment, the present invention provides a composition for enhancing muscle or heart comprising the TRIM72 mutant protein or the gene encoding for the same. It is first elucidated in the present invention that the TRIM72 mutant is a dominant negative form of TRIM72 and proposed that it can enhance muscle differentiation and hypertrophy, thereby strengthening muscle or heart.

In the composition for enhancing muscle or heart of the present invention, the gene may be inserted in an animal cell expressing vector, more preferably an adenoviral vector. For the plasmid vector, pCMV-Flag or pHM6-HA vector may be used. And, for the adenoviral vector, pAd/CMV/V5-DEST (Invitrogen) may be used.

In another embodiment, the present invention provides an animal cell expressing vector comprising the TRIM72 mutant gene.

The animal cell expressing vector may be an adenoviral vector.

In another embodiment, the present invention provides a virus clone obtained by packaging an adenoviral vector comprising the TRIM72 mutant gene in 293T cells.

In another embodiment, the present invention provides animal cells transformed by the animal cell expressing vector comprising the TRIM72 mutant gene.

In another embodiment, the present invention provides a TRIM72 promoter in which the E2 or E3 box is truncated or mutated from a base sequence of any of SEQ ID NOS: 6 to 8. The base sequences of SEQ ID NOS: 6 to 8 are those of TRIM72 promoters comprising the domains 1269 bp, 1144 by and 883 bp, respectively, upstream of the ATG start codon.

The mutant TRIM72 promoter of the present invention may be one in which the E2 box, which corresponds to 557th through 562nd upstream of the start codon, or the E3 box, which corresponds to 580th through 585th upstream of the start codon, is truncated or mutated.

The TRIM72 promoter may have a base sequence of SEQ ID NO: 9 or 10. SEQ ID NO: 9 is that of an 883 by TRIM72 promoter in which the E2 box is mutated, and SEQ ID NO: 10 is that of an 883 by TRIM72 promoter in which the E3 box is mutated.

Because the TRIM72 proposed by the inventors negatively controls the growth of muscle, cattle with large muscle mass may be produced by knocking out the TRIM72 gene. Also, cattle with large muscle mass may be produced by inducing transgenic cattle overexpressing the mutant ΔRING TRIM72 or C14A TRIM72.

The pharmaceutical composition of the present invention may be administered along with a physiologically acceptable vehicle. For oral administration, a binder, glidant, disintegrant, excipient, solubilizer, dispersant, stabilizer, suspender, pigment, perfume, etc. may be used. For injection, a buffer, preservative, pain reliever, solubilizer, tonicity agent, stabilizer, etc. may used. For local administration, a base, excipient, preservative, etc. may used.

The pharmaceutical composition of the present invention may be prepared into various formulations along with the aforementioned pharmaceutically acceptable vehicles. To take oral administration for example, it may be prepared into tablet, troche, capsule, elixir, suspension, syrup, wafer, or the like. For injection, it may be prepared into a single administration ampule or multiple administration form. Besides, the pharmaceutical composition of the present invention may be prepared into various formulations according to the method commonly used in the related art.

The pharmaceutical composition of the present invention may be orally or parenterally, e.g., intravenously, subcutaneously, intranasally or intra-abdominally, to human and animals. Parenteral administration may be carried out by injection, e.g., subcutaneous injection, intramuscular injection and intravenous injection, or dropping.

The effective dose of the TRIM72 gene, TRIM72 protein or its inhibitor included in the pharmaceutical composition of the present invention may vary dependent on sex, severity of disease, age, route of administration, target cells, degree of expression, and the like, and may be easily determined by those skilled in the art. For example, the effective dose may be from about 0.01 ug/kg to about 100 ug/kg.

DESCRIPTION OF DRAWINGS

The patent or application file contains at least one drawing executed in color. Copies of this patent or patent application publication with color drawing(s) will be provided by the Office upon request and payment of the necessary fee.

FIG. 10 shows that deletion of the RING domain or substitution of cystine in the RING domain with alanine promotes muscle differentiation. A. TRIM72 has a consensus sequence in the RING domain binding with $Zn^{2+}$. B. Wild type TRIM72, ΔRING TRIM72 and C14A TRIM72 genes were transfected into C2C12 myoblasts and differentiation into myotubes was induced. Wild type TRIM72 inhibited muscle differentiation, whereas C14A TRIM72 and ΔRING TRIM72 enhanced muscle differentiation as compared to other neighboring cells.

BEST MODE

Figure 1:
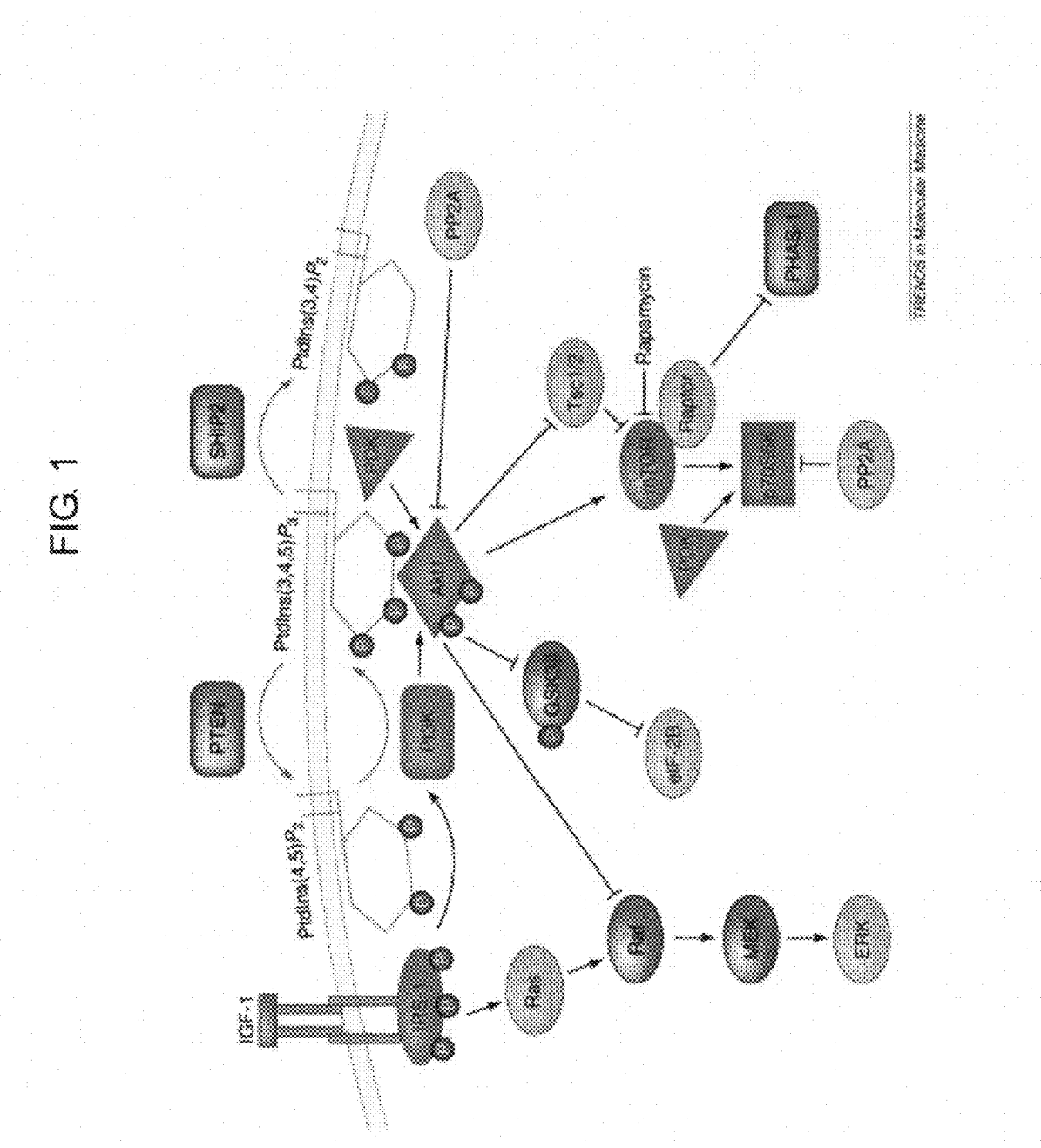
FIG. 1 illustrates the PI3K-AKT and Ras-Raf-MEK-ERK signaling pathway induced by IGF in muscle differentiation and hypertrophy.

Practical and presently preferred embodiments of the present invention are illustrated as shown in the following Examples. However, the present invention is not restricted to the following Examples, and many variations are possible within the spirit and scope of the present invention.

Example 1

Cell Culture, Animal and Antibodies

C2C12 cells were purchased from ATCC and grown in Dulbecco's modified Eagle's medium (DMEM) supplemented with 2% penicillin/streptomycin (WelGene) and 10% fetal bovine serum (WelGene) in a 5% $CO_2$ incubator at 37° C. Confluent C2C12 myoblasts were differentiated into myotubes by incubation with DMEM supplemented with the same antibiotics and 2% horse serum. Every 48 hours, the myotubes were fed with fresh DMEM containing 2% horse serum. Male C57BL/Ksj mice were maintained on a controlled lighting schedule, with a 12-h dark period. Twenty-week-old mice were used in all of the experiments in this study.

Anti-TRIM72 rabbit polyclonal and mouse monoclonal antibodies were generated according to the laboratory manual and by AbFrontier (Korea), respectively. Anti-IRS-1 (Upstate and BD Transduction Laboratories), IGF-IR☐ (Santa Cruz), PI(3)K p85 (Upstate), Myc (Santa Cruz), Flag (Sigma and Santa Cruz), HA (Santa Cruz) and His (Amersham Biosciences) antibodies were used for immunoprecipitation. Anti-myogenin (BD Transduction Laboratories), MyoD (BD Transduction Laboratories and Santa Cruz), caveolin-3 (Santa Cruz), myosin heavy chain (Sigma and Developmental Studies Hybridoma Bank), myostatin (R&D systems), Myf5 (Santa Cruz), Akt (Upstate), pAkt (S473, Cell Signaling Technology), MAPK (Santa Cruz), pMAPK (Santa Cruz), phosphotyrosine (BD Transduction Laboratories), ubiquitin (Santa Cruz) and ☐-actin (Sigma) antibodies were used for immunoblottings.

Example 2

Two-Dimensional Electrophoresis (2-DE) of Detergent-Resistant Lipid Rafts

Four 150 mm dishes of C2C12 myoblasts and myotubes were mixed with 1 ml of lysis buffer (25 mM HEPES pH 6.5, 1% Triton X-100, 150 mM NaCl, 1 mM EDTA, 1 mM PMSF, and protease cocktail), homogenized 20 times with a tight Dounce homogenizer (Kontes), and incubated for 30 min at 4° C. The extract was mixed with 1 ml of 2.5 M sucrose, transferred to a SW41 centrifuge tube, and overlaid with 6 ml of 30% sucrose solution and 4 ml of 5% sucrose solution containing 25 mM HEPES pH 6.5, and 150 mM NaCl. The discontinuous sucrose gradients were centrifuged for 18 h at 4° C. at 39,000 rpm. The gradient was fractionated into 12 fractions from the bottom to the top. The lipid raft fractions were washed with washing buffer (25 mM HEPES pH 7.4, 150 mM NaCl) by ultracentrifugation (20,000 rpm, 30 min, 4° C.), and suspended with 100 µl of resuspension buffer (9 M urea, 2 M thiourea, 4% CHAPS, protease cocktail and 1 mM EDTA). 2-DE, in-gel protein digestion and electrospray ionization tandem mass spectrometry (ESI-MS/MS) were performed as previously described [Kim, K. B. et al. Proteomics 6, 2444-53 (2006)].

Example 3

Adenovirus Preparation and Infection

An adenoviral vector with TRIM72 was constructed using ViraPower™ Adenoviral Expression System (Invitrogen) under control of the cytomegalovirus (CMV). Full-length-TRIM72 ORF (open reading frame) was cloned into an entry vector pENTR (Invitrogen) using the restriction enzyme sites (SalI and NotI) and homologously recombined into a destination vector pAd/CMV/V5-DEST (Invitrogen) which has the adenoviral genome and CMV promotor. The cloned TRIM72-adenoviral genome was linearized by cutting with PacI restriction enzyme and transfected into 293A cells using a transfection agent (GenePorter II). After 10-15 days of the transfection, the supernatant comprising adenovirus was re-transfected into 293A cells to obtain the amplified adenovirus. The obtained adenovirus supernatant was purified into adenovirus particles using cessium chlororide. C2C12 myoblasts grown in 6 well plates were infected by adenovirus with the dosage of $4 \times 10^{10}$ VP/ml.

Example 4

Plasmids, Transient Transfection, and Luciferase Assay

IRS-1 constructs (full-length, 1-3729; PH-PTB domain, 1-900; Mid-region, 880-2608; Rear-region, 2581-3729) and TRIM72 cDNA constructs (full-length, 1-1431; ΔRING, 181-1431; coiled-coil, 367-1020; CCSPRY, 367-1431; SPRY, 687-1431; Δcoiled-coil) were generated by PCR using the primers described in Table 1 and cloned into pCMV-Tag2B vector and pCMV-3Tag4a vector (Stratagene), respectively. Alternatively, TRIM72 and TRIM72 C14A were generated by PCR reaction using the primers described in Table 1 and cloned into pHM6-HA vector, pCMV-Tag2B or pHM6 vector (Roche). For TRIM72 promoter, 1269 bp, 1144 by and 883 by upstream regions from ATG start codon were amplified by PCR reaction using the primers described in Table 1. Site-directed mutagenesis of E2 and E3 boxes in 883 by fragment was performed by PCR reaction using the primers described in Table 1. These constructs were inserted into pGL3basic vector (Promega). The coding regions of mouse MyoD, Myf5, Myogenin and Mrf4 regions were amplified by PCR and cloned into pcDNA3 vector (Invitrogen). Gene transfection was performed by using Geneporter (Genlantis) or Lipofectamin (Invitrogen) according to manufacturer's protocol. Luciferase activity in cell lysates was measured by using the luciferase assay system (Promega) in a Luminoskan Ascent (Thermo Labsystem). We normalized the relative luciferase activity to the activity of co-expressed β-galactosidase.

TABLE 1

Sequences of Primers used in PCR reactions

| Amplification Target | | Sequences of Primers | Rest. Enz. |
|---|---|---|---|
| IRS-1 construct | full-length, 1-3729 | Forward: GAATTCATGGCGAGCCCTCCGGAGAGCGAT | EcoRI |
| | | Reverse: GTCGACCTACTGACGGTCCTCTGGCTGGCTTCTG | SalI |
| | PH-PTB domain, 1-900 | Forward: GAATTCATGGCGAGCCCTCCGGAGAGCGAT | EcoRI |
| | | Reverse: GTCGACGGTCAGCCCCACCTGGCTGGG | SalI |
| | Mid-region, 880-2608 | Forward: GAATTCCCCAGCCAGGTGGGGCTGACC | EcoRI |
| | | Reverse: GTCGACTGCTGGCCTTGGGATCCCCCAGGGACAGCTTC | SalI |
| | Rear-region, 2581-3729 | Forward: GAATTCCTGTCCCTGGGGGATCCCAAGGCCAGCACCTT | EcoRI |
| | | Reverse: GTCGACCTACTGACGGTCCTCTGGCTGGCTTCTG | SalI |
| TRIM 72 cDNA construct | full-length, 1-1431 | Forward: GAATTCATGTCGGCTGCGCCCGGCCTC | EcoRI |
| | | Reverse: GGATCCGGCCTCGGCGCCTTCGGGACC | BamHI |
| | ΔRING, 181-1431 | Forward: GAATTCCGGCCGCAGGCACTCAGCACC | EcoRI |
| | | Reverse: GGATCCGGCCTCGGCGCCTTCGGGACC | BamHI |
| | coiled-coil, 367-1020 | Forward: GAATTCGCCGAGGCCCACGCACGCCTC | EcoRI |
| | | Reverse: GGATCCGAGCTGCTGGTGCGCCACCAC | BamHI |
| | CCSPRY, 367-1431 | Forward: GAATTCGCCGAGGCCCACGCACGCCTC | EcoRI |
| | | Reverse: GGATCCGGCCTCGGCGCCTTCGGGACC | BamHI |
| | SPRY, 687-1431 | Forward: GAATTCCCGCAGACTGAGTTCCTCATG | EcoRI |
| | | Reverse: GGATCCGGCCTCGGCGCCTTCGGGACC | BamHI |
| | Δcoiled-coil (397-696 deletion) | Front_Forward: GAATTCATGTCGGCTGCGCCCGGCCTC | EcoRI |
| | | Front_Reverse: CTCAGTCTGCGGCTGTGTCTTGAGGCGTGC | |
| | | Rear_Forward: CTCAAGACACAGCCGCAGACTGAGTTCCTC | BamHI |
| | | Rear_Reverse: GGATCCGGCCTCGGCGCCTTCGGGACC | |
| | TRIM72 C14A | Forward: GAATTCATGTCGGCTGCGCCCGGCCTCCTGCACCAGGAG CTGTCCGCCCCGCTGTGCCTG | EcoRI |
| | | Reverse: GGATCCGGCCTCGGCGCCTTCGGGACC | BamHI |
| TRIM 72 promoter | 1269 bp | Forward: AAAGGTACCGAGCTTTGCAATATCTGG | KpnI |
| | | Reverse: CAGCAAGCTTGGTGAGCCTGGGAAGAGG | HindIII |
| | 1144 bp | Forward: GCCGGTACCGGAATAAATTGTAGGTCA | KpnI |
| | | Reverse: CAGCAAGCTTGGTGAGCCTGGGAAGAG | HindIII |

TABLE 1-continued

Sequences of Primers used in PCR reactions

| Amplification Target | Sequences of Primers | Rest. Enz. |
|---|---|---|
| 883 bp | Forward: CCAGGTACCGAGTTAGCACCATTAGCG | KpnI |
|  | Reverse: CAGCAAGCTTGGTGAGCCTGGGAAGAGG | HindIII |
| E2 and E3 boxes Site-directed mutagenesis | E3mutant: |  |
|  | Forward: CCACTATATGCCTATAACCTTTTGCATCCACCCACT | KpnI |
|  | Reverse: AGTGGGTGGATGCAAAAGGTTATAGGCATATAGTGG |  |
|  | E2mutant: |  |
|  | Forward: GCATCCACCCACTGCAATCTTGCCCTGAATCCC | HindIII |
|  | Reverse: GGGATTCAGGGCAAGATTGCAGTGGGTGGATGC |  |

Example 5

RNA Interference

SiRNA oligomer targeting TRIM72 was designed from Dharmacon. Target sequence of TRIM72 is 5'-AAGCACGC-CUCAAGACACAGC-3'. The cell cultures were transfected with control RNAi and TRIM72 specific siRNA using transfection reagent (TransIT®-TKO, Mirus), which was prepared according manufacturer's instruction. Transfected cells were then transferred to media containing 2% horse serum at least for 48 h.

Example 6

Western Blotting, Immunoprecipitation and Immunostaining

Western blotting and immunostaining were performed as described in Kim, K. B. et al. Proteomics 6, 2444-53 (2006). For immunoprecipitation, cells were lysed in buffer containing 20 mM Tris-HCl pH 7.4, 137 mM NaCl, 1 mM $MgCl_2$, 1 mM $CaCl_2$, 20 mM NaF, 10 mM $Na_4P_2O_7$, 1% NP-40, 1 mM $Na_3VO_4$, 1 mM PMSF and protease inhibitor cocktail (Roche). The whole cell lysates (600 μg protein) were incubated with specific antibodies for 90 min and then with 50 μl of Protein A-sepharose or G-agarose bead (50%) slurry for 1 h. The immunoprecipitates were analyzed by Western blotting.

Example 7

Northern Blotting

Premade Northern blot (MTN™) containing approximately 2 μg of poly A+ RNA per lane from eight different mouse tissues was purchased from Clontech. After prehybridization, [$α^{32}$P]-labeled TRIM72 probe (789-1419 by fragment) produced by random priming (TaKaRa) was incubated for 2 h at 68° C. in the hybridization solution in kit. Hybridized blot was washed, dried and exposed to image plate. Recorded signal was imaged by BAS Reader (BAS-25000, Fuji Photo Film).

Example 8

RT-PCR

Total RNA was extracted from the C2C12 myoblast and myotubes and single stranded cDNA was synthesized using reverse transcriptase (MMLV, Invitrogen) and random primers. The expression level of the TRIM72 during differentiation and in various tissues was examined by semi-quantitative PCR. The following forward and reverse primer pairs were used for specific amplification:

5'-TCCCTGTTGTCAGGCATCTAC-3'
and

5'-TTCTTCCACACCTGGAATTTG-3'
for TRIM72,

5'-GCTCAGCTCCCTCAACCAG-3'
and

5'-ATGTGAATGGGGAGTGGGA-3'
for myogenin,

5'-CTCCTTTGAGACAGCAGACGACTT-3'
and

5'-AAATCGCATTGGGGTTTGAGCCTG-3'
for Myo D,

5'-AGGACATTCACTGCAAGGAGA-3'
and

5'-CAGAAGGTGCGGATACACAGT-3'
for caveolin-3,

5'-AGAAGGAGGAGGCAACTTCTG-3'
and

5'-ACATACTCATTGCCGACCTTG-3'
for MHC,

5'-TGTCAGAGTCTAGGGGAATTGG-3'
and

5'-AGGTTTGGAGACTGGGAGAG-3'
for p21,
and

5'-GAAGAGCTATGAGCTGCCTGA-3'
and

5'-CTCATCGTACTCCTGCTTGCT-3'
for β-actin.

Example 9

Chromatin Immunoprecipitation

Formaldehyde-fixed C2C12 myoblasts and myotubes were lysed with buffer containing 0.5% NP-40, 5 mM PIPES and 85 mM KCl pH 8.0. After brief microcentrifugation for 5 min at 5,000 rpm, the pellet was further incubated with nuclear lysis buffer containing 50 mM Tris-HCl pH 8.0, 1% SDS, and 10 mM EDTA, sonicated and centrifuged for 5 min at 5,000 rpm. The supernatant was used in ChIP assay by using anti-MyoD antibody as described in Wilson, E. M., and Rotwein, P. J. Biol. Chem. 281, 29962-29971 (2006). The immunoprecipitates were amplified by PCR with primers. The forward and reverse primers were 5'-AGGGAGTGGGTAGGACAGCTAAATAT-3' and 5'-CAGGCTCAATGCAAGGGCAGGGA-3', respectively.

Example 10

The Measurement of PI(3)K Activity

The immunoprecipitates with anti-p85 antibody were washed twice with buffer A (20 mM Tris-HCl pH 7.4, 137 mM NaCl, 1 mM $MgCl_2$, 1 mM $CaCl_2$, 20 mM NaF, 10 mM $Na_4P_2O_7$, 1% NP-40, 3 mM benzamidine, 1 mM $Na_3VO_4$, and protease inhibitor cocktail) and once with the PI(3)K reaction buffer (10 mM Tris-HCl pH 7.4, 100 mM NaCl, 1 mM EDTA and 1 mM sodium vanadate) and suspended in 50 µl of reaction buffer containing 60 µg of phosphoinositide (PI, Sigma) and 20 µCi [$\gamma$-$P^{32}$]. The phosphorylated lipids were separated by TLC as described in Ueki, K., et al. Mol Cell Biol 20, 8035-46 (2000).

Example 11

IRS-1 Ubiquitination 293T cells are transfected with pCMV-HA-TRIM72 (1 µg) or pCMV-HA-TRIM72 C14A (1 µg) and pCMV-Flag-IRS-1 (3 µg) and His-ubiquitin (3 µg) using Polyfect (Qiagen). Twenty-four hours after transfection, cells were treated with MG132 (5 µM) for 12 h. Cell lysates were immunoprecipitated with anti-Flag for 2 h. The immunoprecipitates were analyzed by Western blotting against anti-His antibody.

Result 1: TRIM72 is Found in Lipid Rafts of Skeletal Muscle Cells.

Insulin-like growth factors I and II (IGF-I and IGF-II) are essential for skeletal muscle development, hypertrophy and regeneration [Glass, *Trends Mol. Med.*, 9, 344, 2003; Glass, *Nat. Cell Biol.*, 5, 87, 2003]. Skeletal precursor stem cells, which are satellite cells, lose their muscle differentiation activity when treated with anti-IGF-II antibody or anti-sense IGF-II, whereas IGF-I overexpression in mice leads to significantly increased muscle mass and force generation [Musaro, *Nat. Genet.*, 27, 195, 2001; Erbay, *J. Cell Biol.*, 163, 931, 2003; Wilson, 281, 29962, 2006; Wilson, 282, 5106, 2007]. IGF-I and IGF-II transducer cellular signaling via the IGF-I receptor (IGFR) which subsequently recruits insulin receptor substrate-1 (IRS-1). The recruited IRS-1 activates PI3K-AKT and Ras-Raf-MEK-ERK signaling pathway pathways (FIG. 1). The Ras-Raf-MEK-ERK pathway controls muscle fiber type whereas the PI3K-AKT pathway induces muscle differentiation and hypertrophy [Rommel, 286, 1738, 1999; Murgia, 2, 142, 2000]. The activated AKT induces phosphorylation of mTOR, GSK3l3 and FOXO, thereby stimulating muscle differentiation and suppressing muscular atrophy [Bodine, *Nat. Cell Biol.*, 3, 1014, 2001; Rommel, *Nat. Cell Biol.*, 3, 1009, 2001; Hriba, *J. Cell Biol.*, 162, 535, 2003; Sandri, *Cell*, 117, 399, 2004].

Figure 2A:
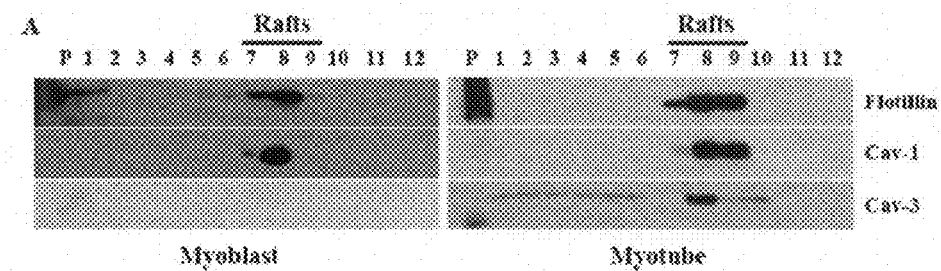
FIG. 2 shows proteins expressed in lipid rafts of myotubes. A. Lipid rafts were isolated from myoblasts and myotubes utilizing their insolubility in detergent and low density. Following sucrose gradient ultracentrifugation, each fraction was immunoblotted. Cav-1=Caveolin-1; Cav-3=Caveolin-3. B. Lipid raft proteins of myoblasts and myotubes were compared by two-dimensional electrophoresis. Protein spots expressed well in the lipid rafts of myotubes were denoted by circles. These protein spots were identified by Q-TOF. C. The portions corresponding to TRIM72 were compared in myoblasts and myotubes (the box in FIG. 2B).
Figure 2B:
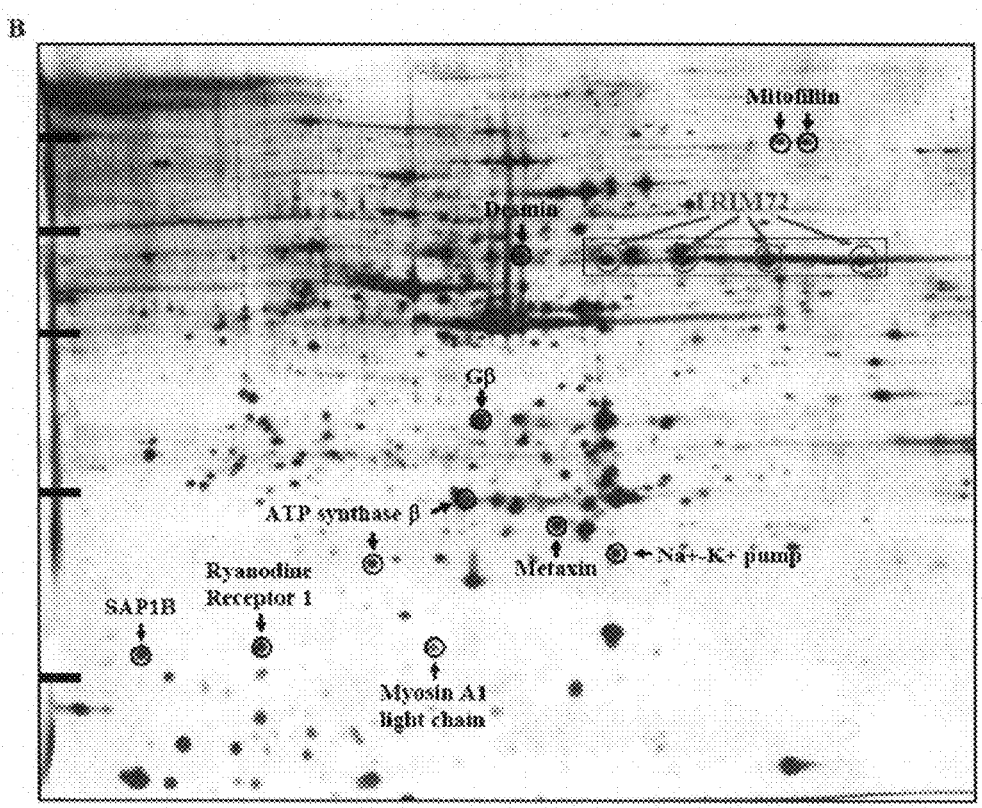
Figure 2C:
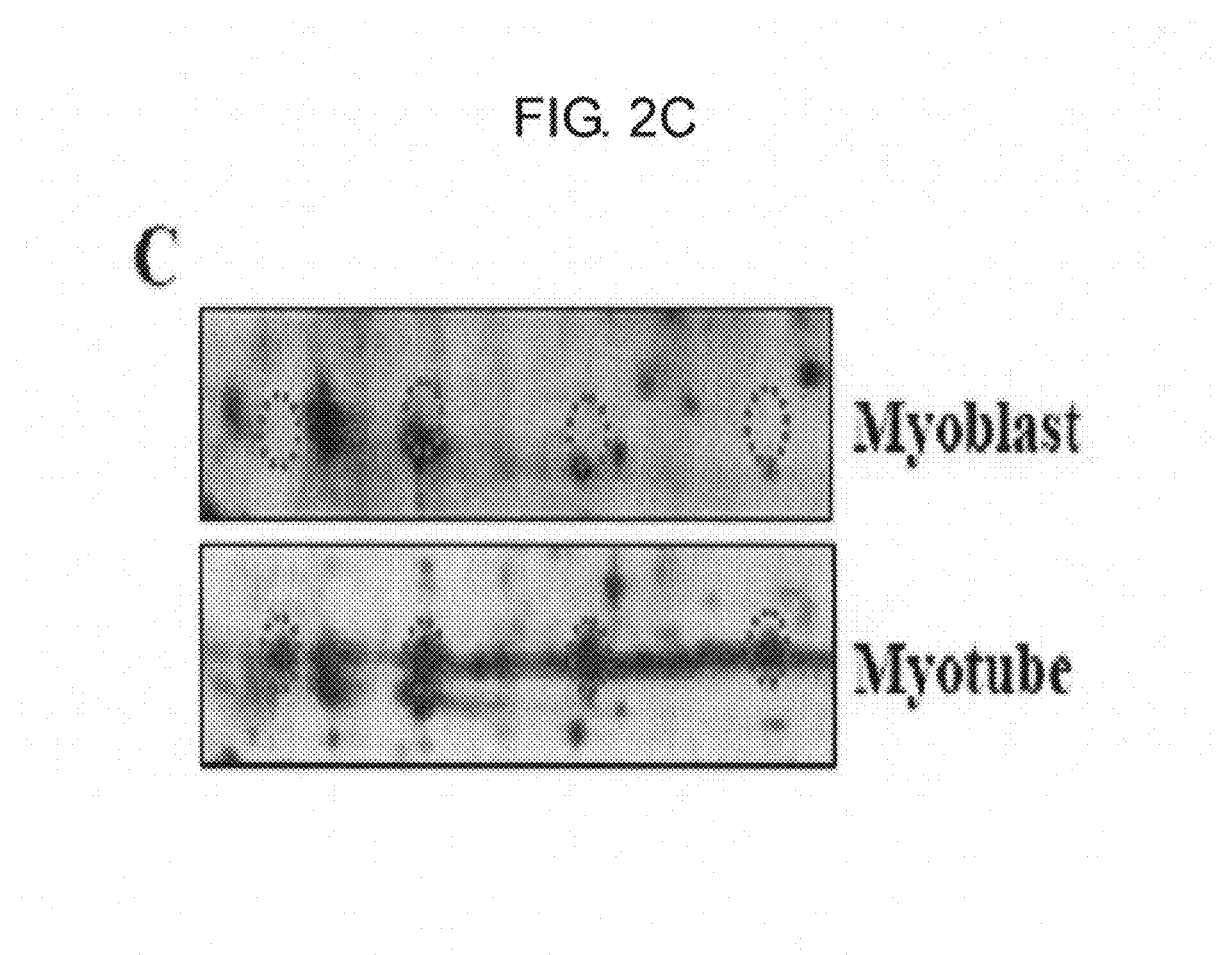
Figure 3A:
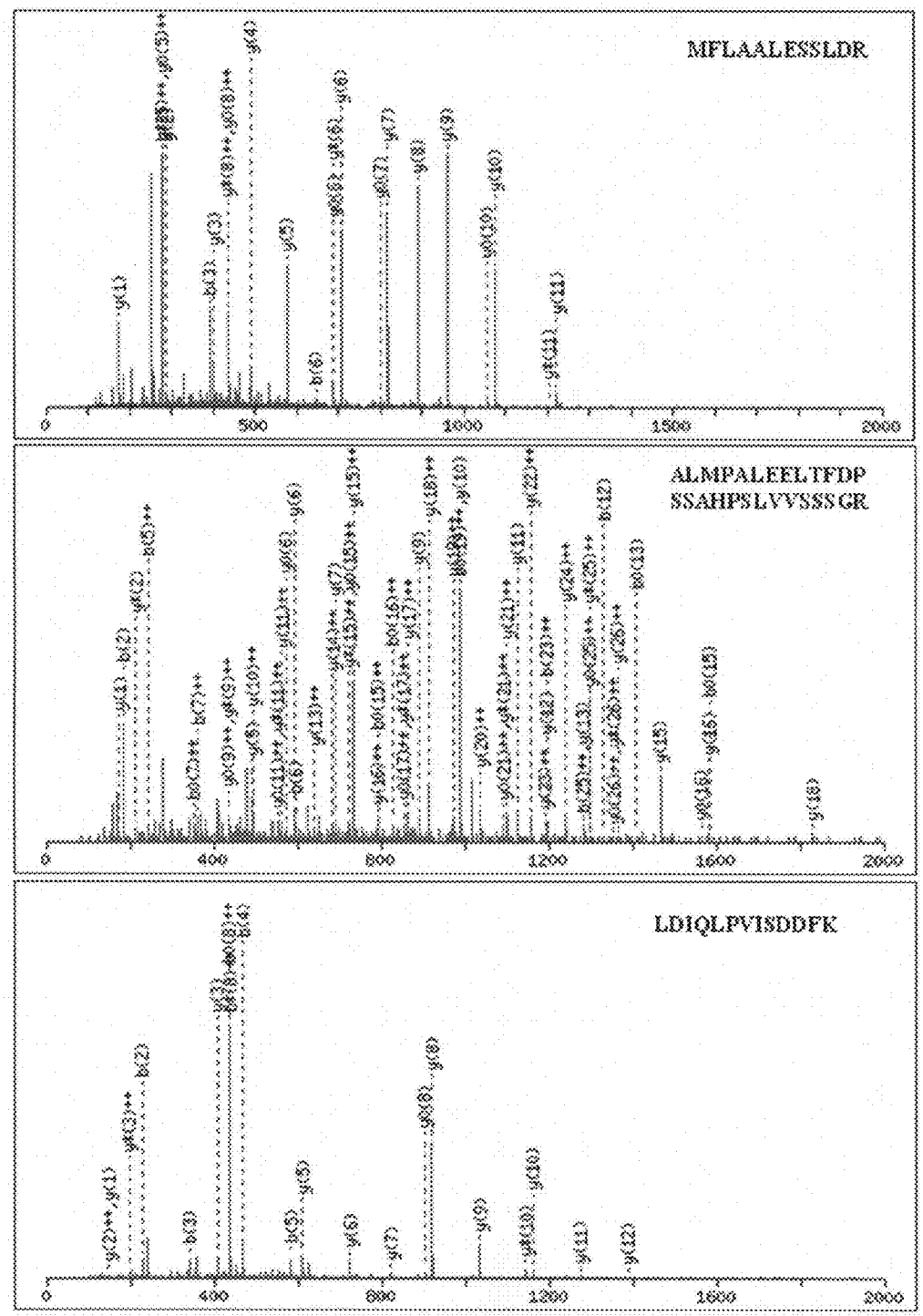
FIG. 3 shows identification result for TRIM72 specifically expressed in lipid rafts of myotubes. A. Mass analysis pattern of the protein corresponding to the box in FIG. 2B obtained by Q-TOF/MS and its amino acid sequence. B. Full-length amino acid sequence of TRIM72. Bold characters denote the amino acid sequence analyzed by Q-TOF/MS, red line denotes RING domain, blue line denotes B box, green line denotes coiled-coil domain, and black line denotes SPRY domain. C. TRIM72 has one RING domain, one B-box, one coiled-coil domain, and one SPRY domain.

Lipid rafts might play a crucial role in skeletal muscle differentiation and hypertrophy because they enrich IGF signaling molecules such as IGFR, IRS-1, PI3K, AKT and GSK3β [Huo, *J. Biol. Chem.*, 278, 11561, 2003; Panetta, *Biochem. Biophys. Res. Commun.*, 316, 240, 2004; Arcaro, *Cell Signal.*, 19, 1081, 2007; Hill, *Curr. Biol.*, 12, 1251, 2002; Sui, *Biochem. Biophy. Res. Commun.*, 345, 1645, 2006]. Thus, novel signaling molecules involved in skeletal muscle differentiation could be discovered by the proteomic analysis of lipid rafts. The inventors isolated detergent-resistant lipid rafts from C2C12 myoblasts and myotubes, based on the Triton X-100 insolubility and low density. C2C12 mononucleated myoblasts were differentiated into multinucleated myotubes by incubating them with 2% horse serum for 2 days. The lipid raft proteins were resolved by two-dimensional electrophoresis and visualized by silver staining. Myotube-specific lipid raft proteins indicated by arrows in two-dimensional electrophoresis profiles (FIG. 2) were identified by Q-TOF/MS. Among these protein spots, four had a molecular weight of 55 kDa and were identified as TRIM72, whose function has never been investigated [FIGS. 2A and 2B]. ID NM 001079932 or [gi|142370482] is mouse TRIM72, and ID NM 001008274 or [gi|142378442] is human TRIM72. FIG. 3A shows the mass spectrum data of TRIM72 identified by Q-TOF/MS, and FIG. 3B shows the amino acid sequence of TRIM72. TRIM72 contains TRIM/RBCC (tripartite motif or N-terminal RING finger/B-box/coiled coil) and SPRY (Spla and Ryanodine receptor) domains (FIGS. 3B and 3C), which are necessary for ubiquitin E3 ligase activity and protein-protein interaction, respectively.

Result 2: TRIM72 is Found in Lipid Rafts of Skeletal Muscle and Heart Muscle.

Figure 4A:
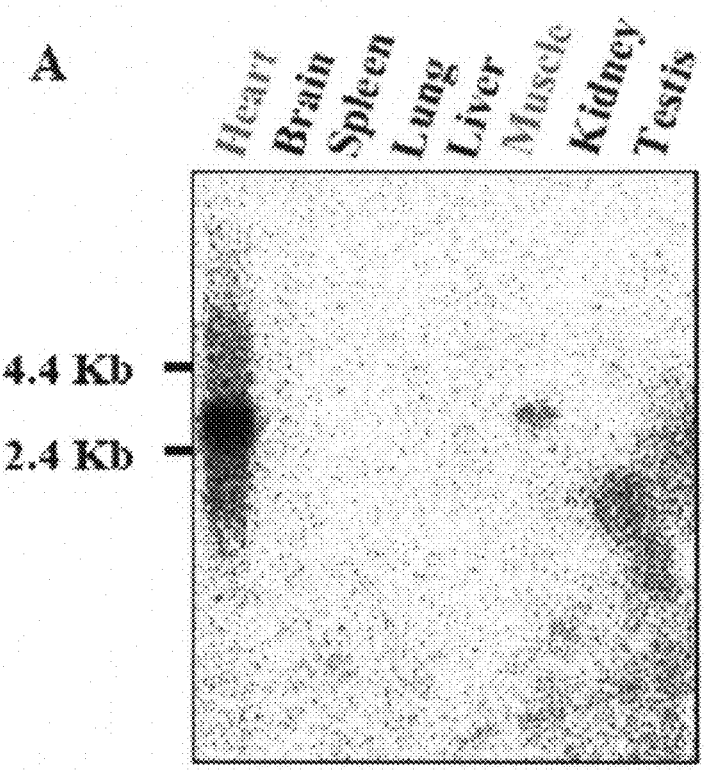
FIG. 4 shows that TRIM72 is specifically expressed only in skeletal muscle and heart muscle. A. mRNAs were extracted from various organs of mouse and subjected to Northern blotting for TRIM72 gene. B. Proteins were extracted from various organs of mouse and subjected to Western blotting using TRIM72 antibody. C. C2C12 myoblasts were differentiated into myotubes and RT-PCR was performed. The amount of mRNA for TRIM72 increased along with the muscle differentiation marker genes caveolin-3 (Cav-3), myogenin, MyoD and myosin heavy chain (MyHC). D. C2C12 cells were differentiated and Western blotting was performed. During muscle differentiation, the amount of TRIM72 protein increased along with other differentiation marker proteins. IRS-1=insulin receptor substrate-1.
Figure 4B:
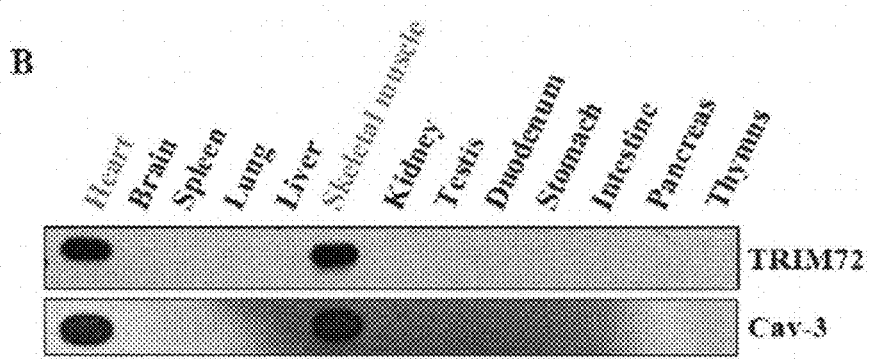
Figure 4C:
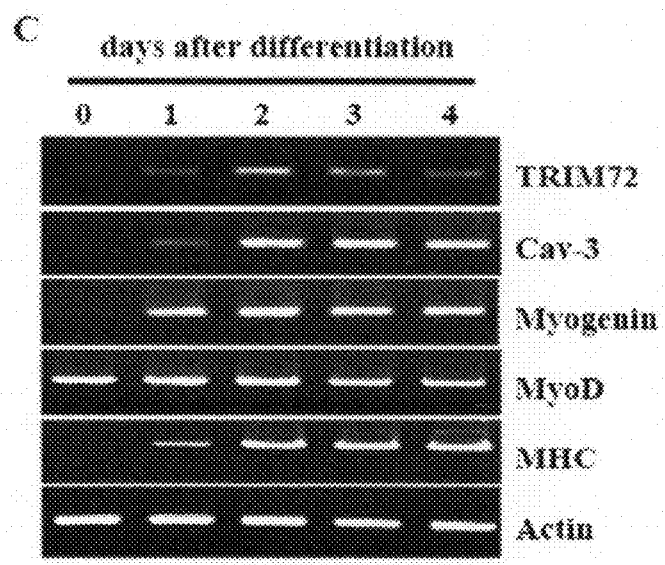
Figure 4D:
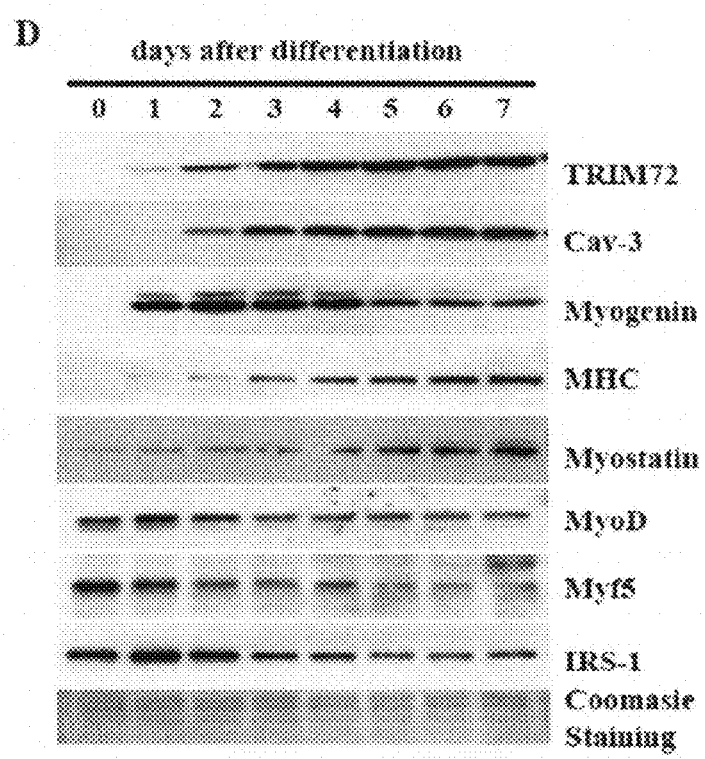
Figure 5A:
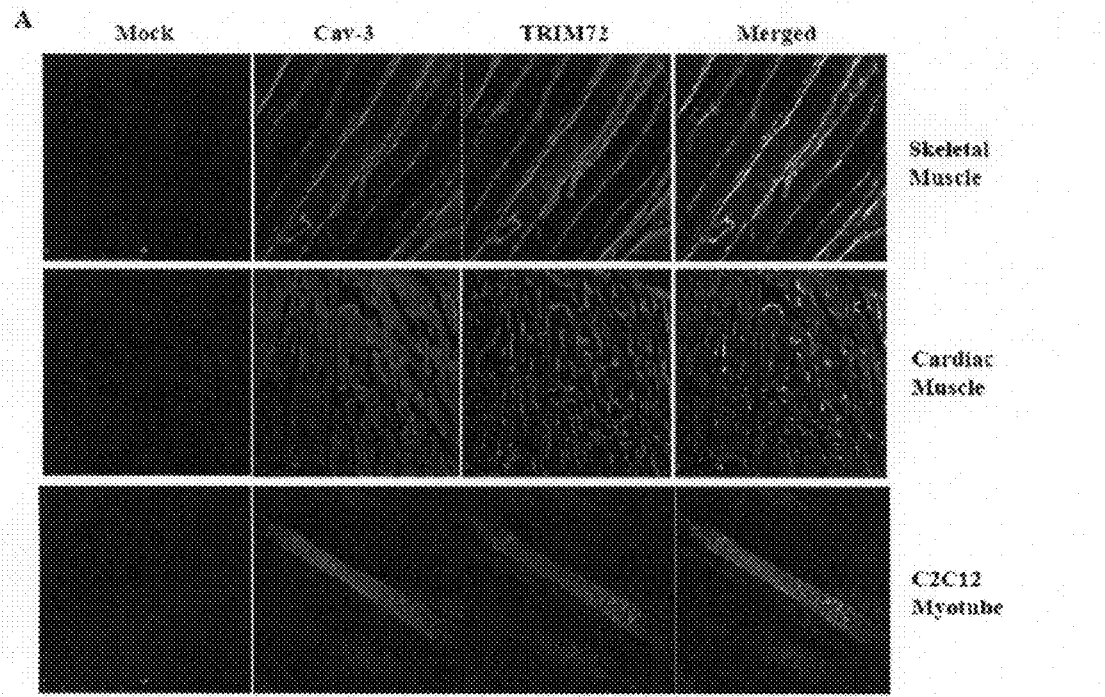
FIG. 5 shows that TRIM72 exists in lipid rafts of sarcolemma. A. TRIM72 and Cav-3 were located in mouse skeletal muscle, heart muscle and C2C12 myotubes by immunofluorescence. B. Cytoplasm and plasma membrane (PM) were separated from mouse skeletal muscle and C2C12 myotubes and subjected to Western blotting using TRIM72 antibody. C. Lipid rafts were separated from mouse skeletal muscle and C2C12 myotubes and subjected to Western blotting using TRIM72 and Cav-3 antibodies. D. At the embryonic stage (E) and postnatal stage (P), the amount of TRIM72 and Cav-3 in heart and skeletal muscle was identified by Western blotting.
Figure 5B:
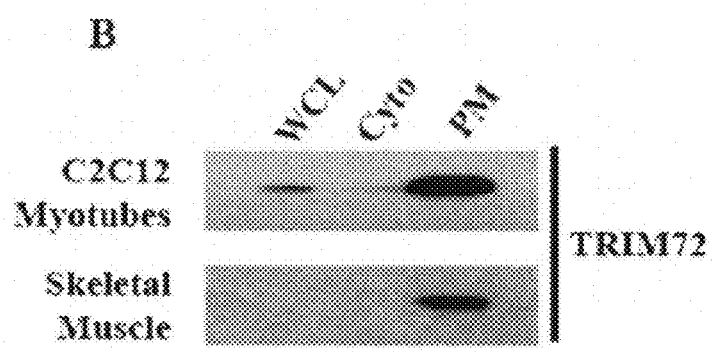
Figure 5C:
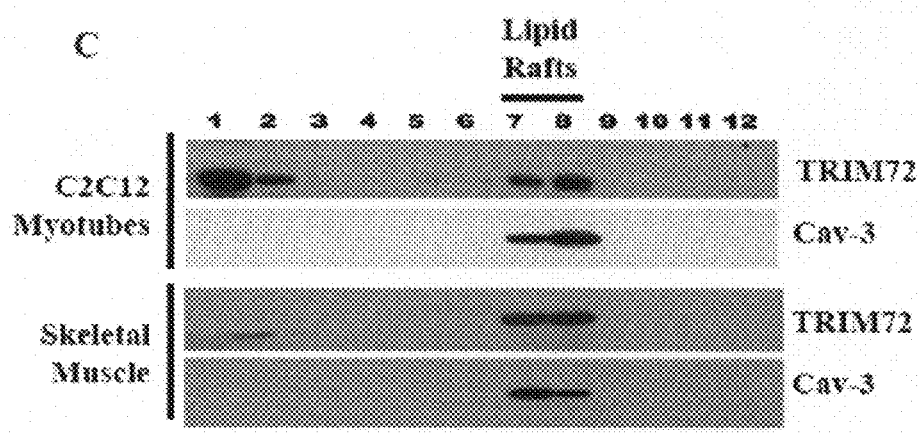
Figure 5D:
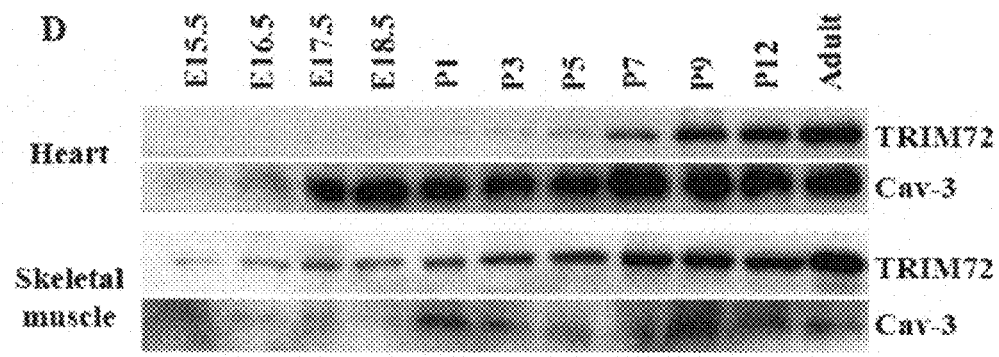

TRIM72 was exclusively expressed in skeletal muscle and heart as determined by Western blotting and Northern blotting (FIGS. 4A and 4B). Further, TRIM72 began to be expressed with myogenesis markers such as myogenin, caveolin-3 and MyHC (myosin heavy chain), as determined by RT-PCR and Western blotting (FIGS. 4C and 4D). TRIM72 was expressed with caveolin-3 in plasma membrane of myotubes and mouse heart and skeletal muscle, as determined by immunofluorescence (FIG. 5A) and was enriched in plasma membrane or lipid rafts (FIGS. 5B and 5C). This indicates that TRIM72 is a lipid raft protein in heart and skeletal muscle. Interestingly, TRIM72 was highly expressed heart and skeletal muscle isolated from the mice in the postnatal stage whereas it was not expressed in the embryonic stage (FIG. 5D). This indicates that TRIM72 is not involved in cardiogenesis and myogenesis in the embryonic stage.

Result 3: TRIM72 Suppresses Muscle Differentiation.

Figure 6A:
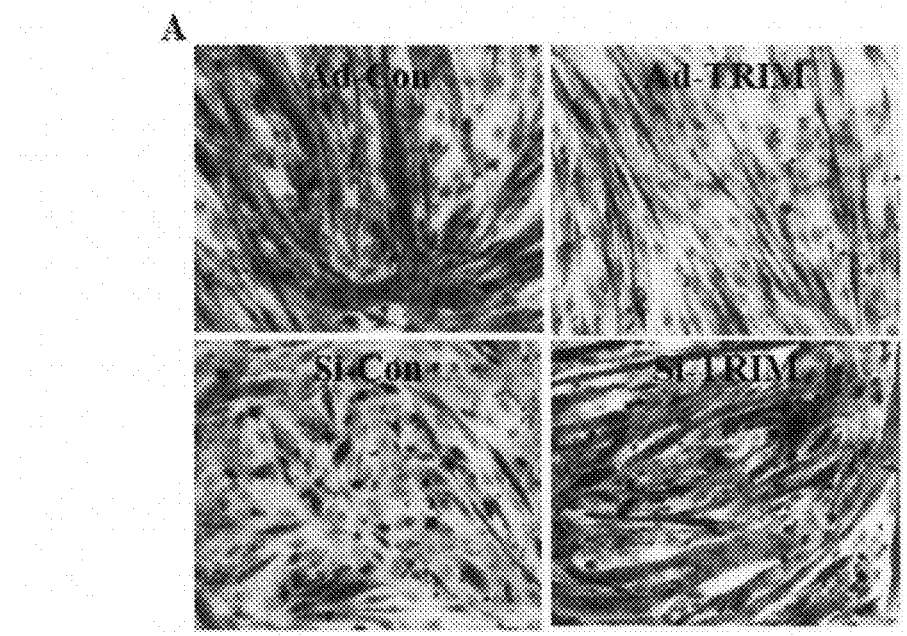
FIG. 6 shows a test result demonstrating that TRIM72 is a negative regulator of muscle differentiation. After overexpressing TRIM72 in C2C12 myoblasts using an adenovirus system or after inhibiting expression of TRIM72 in C2C12 myotubes using SiRNA, the cells were observed after H&E staining (A), MyHC fluorescent staining (B), and Western blotting for TRIM72, Myogenin and Cav-3 (C), and the number of nuclei per each cell was counted (D) to determine the degree of muscle differentiation.
Figure 6B:
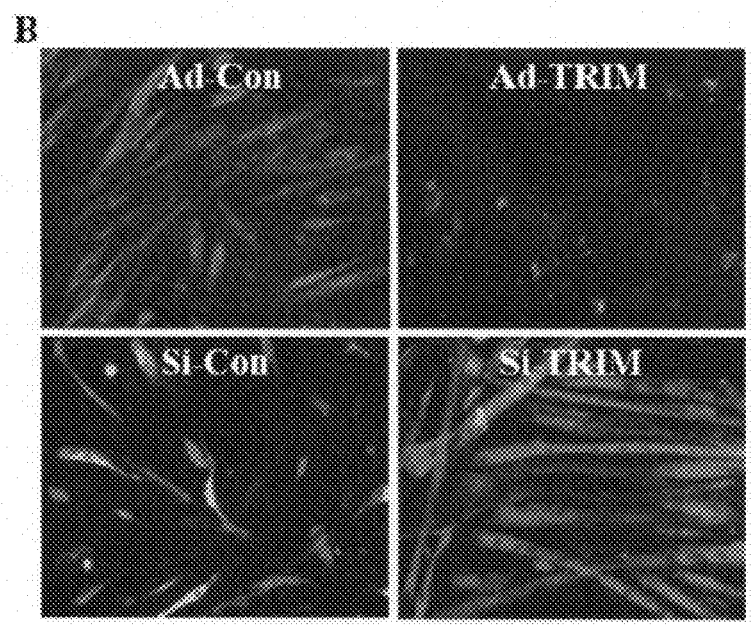
Figure 6C:
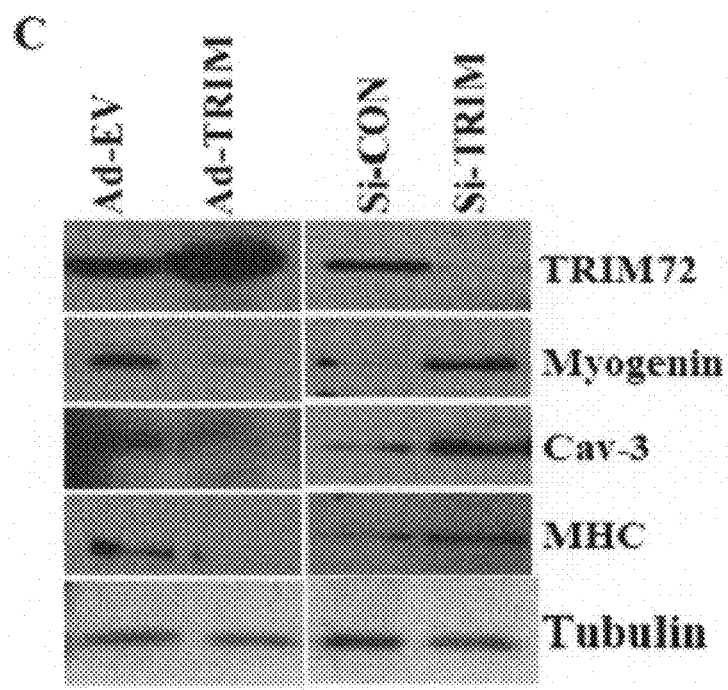
Figure 6D:
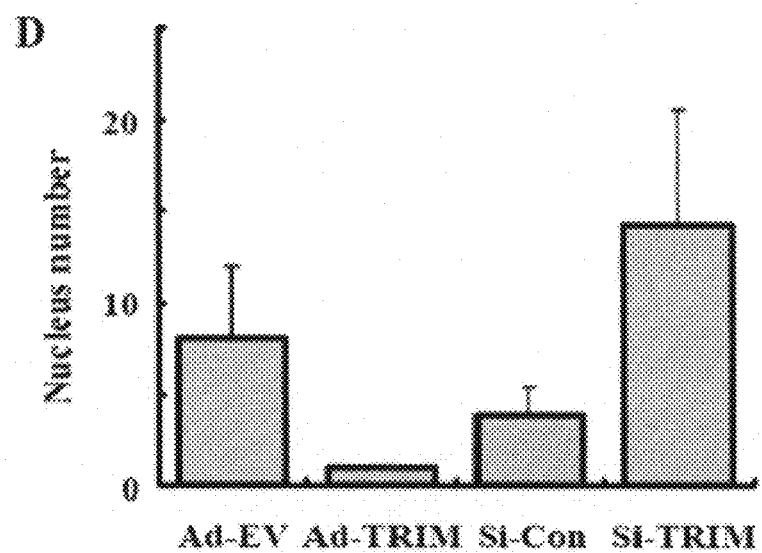

In order to understand the role of TRIM72 in myogenesis, TRIM72 was overexpressed in C2C12 myoblasts by treating with an adenoviral vector or expression of TRIM72 was interfered using SiRNA, and myogenesis was monitored. As shown in FIG. 6A, myogenesis was prevented by TRIM72 overexpression, but enhanced by TRIM72 knockdown. The degree of muscle differentiation can be identified from the degree of MyHC staining. The amount of MyHC decreased when TRIM72 was overexpressed, but it increased rapidly when TRIM72 was knocked down (FIG. 6B). Further, myogenesis was completely prevented by TRIM72 overexpression as determined by the expression level of myogenesis marker proteins (myogenin, caveolin-3 and MyHC), nucleus number per myotubes, and the like (FIGS. 6C and 6D), whereas TRIM72 knockdown enhanced muscle differentiation. This suggests that TRIM72 is a negative regulator in muscle differentiation.

Result 4: TRIM72 Inhibits IGF-1-Mediated Activation of PI3K/AKT.

Figure 7A:
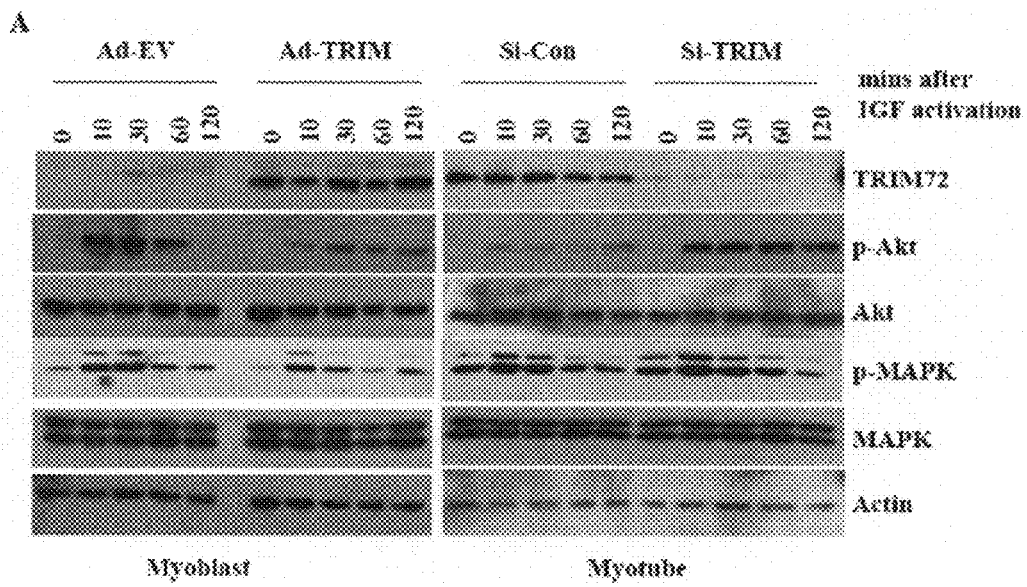
FIG. 7 shows that TRIM72 inhibits IGF-1-induced PI3K/AKT activation. After overexpressing TRIM72 in C2C12 myoblasts or after inhibiting expression of TRIM72 in C2C12 myotubes, AKT and MAPK phosphorylation (A) and PI3K activity (B) induced by IGF were investigated.
Figure 7B:
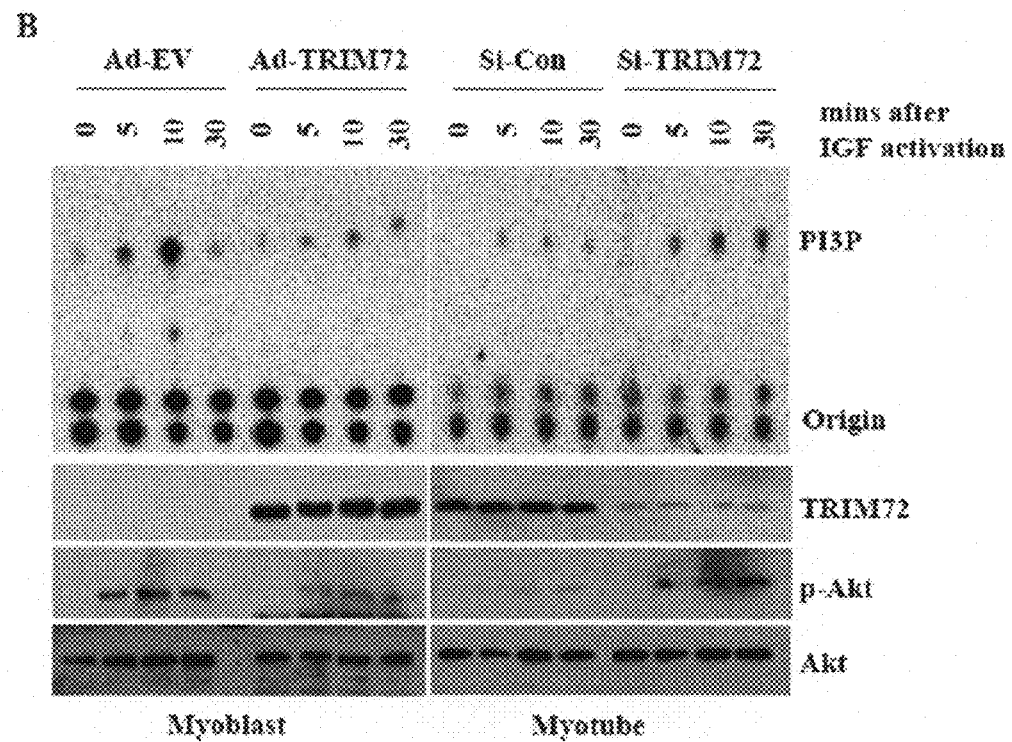

Since IGF is a major growth factor regulating skeletal muscle differentiation and hypertrophy, the possible involvement of TRIM72 in the IGF-1-mediated activation of IGFR/IRS-1/PI3K/AKT activation was investigated after overexpressing or knocking down TRIM72 in myoblasts and myotubes. IGF-1-induced AKT phosphorylation was inhibited by TRIM72 overexpression, but enhanced by TRIM72 knockdown (FIG. 7A), showing that TRIM72 prevented AKT activation. In contrast, IGF-1-induced ERK1/2 phosphorylation was not changed by TRIM72 overexpression or knockdown, suggesting that the IGF-I/IGFR/Raf/MAPK signaling pathway might not be affected by TRIM72. TRIM72 inhibition of IGF-induced AKT phosphorylation prompted the inventors to test the effect of TRIM72 on PI3K activation. FIG. 7B shows that IGF-1-induced PI3K activation was abrogated by TRIM72 overexpression, but enhanced by TRIM72 knockdown. This shows that TRIM72 regulates PI3K activation through the IGF-I/IGFR/IRS-1 signaling pathway.

Result 5: TRIM72 Binds with IRS-1 and Blocks IGF-I Signaling.

Figure 8:
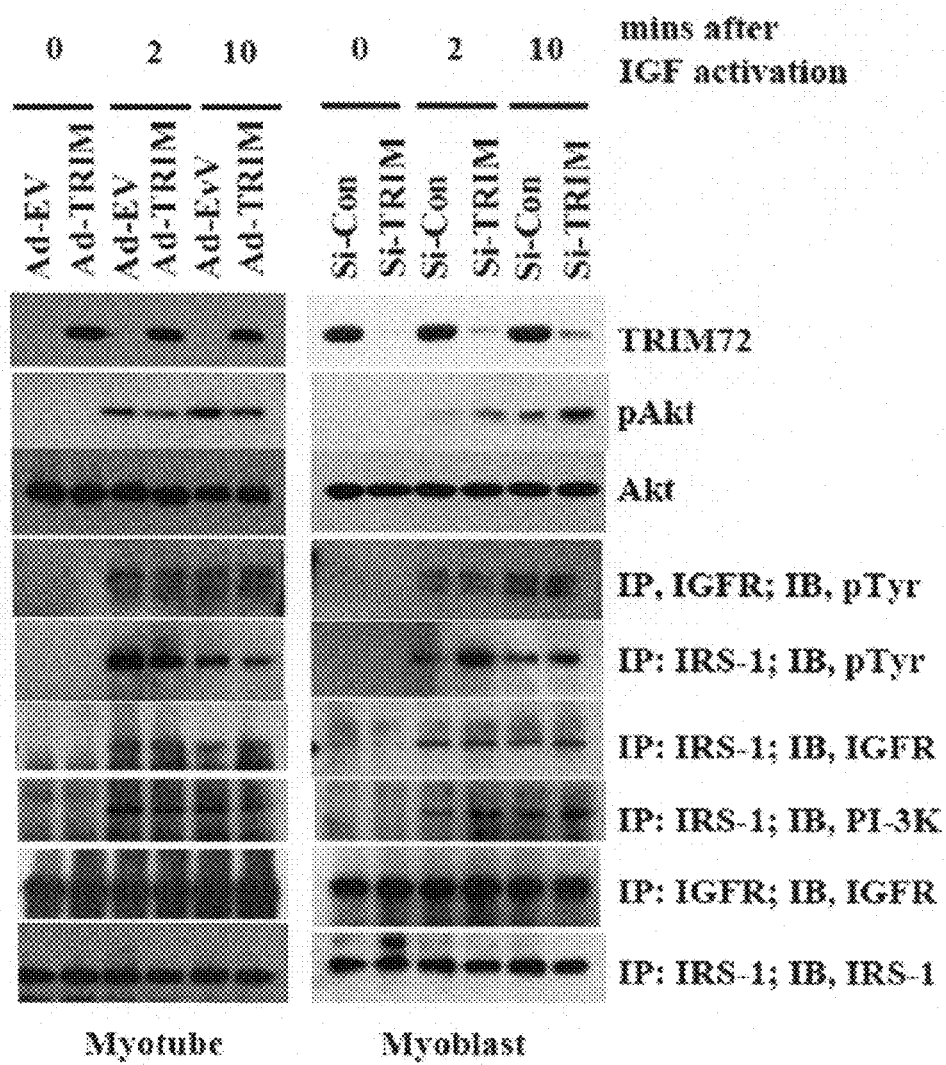
FIG. 8 shows that TRIM72 inhibits IGF-1-induced tyrosine phosphorylation of IRS-1 by binding with IRS-1. After overexpressing TRIM72 in C2C12 myoblasts or after inhibiting expression of TRIM72 in C2C12 myotubes, followed by IGF-I activation, tyrosine phosphorylation of IGFR and IRS-1 and interaction of IGFR and IRS-1 were investigated by immunoprecipitation.
Figure 9A:
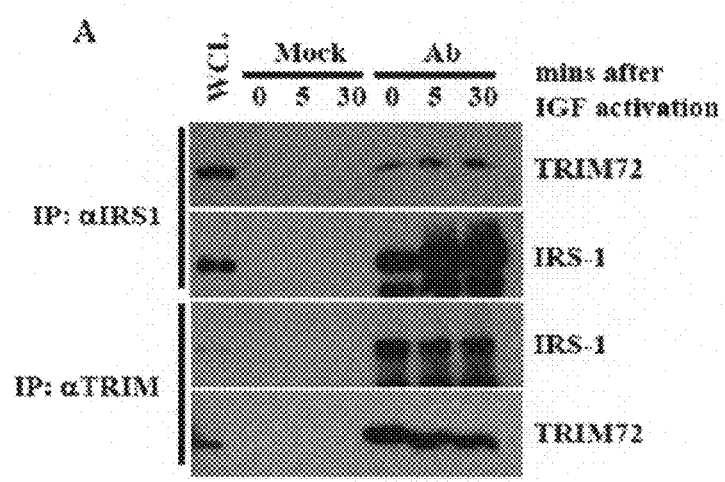
FIG. 9 shows the binding site of TRIM72 and IRS-1. Mid and Rear regions of IRS-1 bind with the coiled-coil domain of TRIM72. A. C2C12 myotubes were treated with IGF-I and binding of IRS-1 and TRIM72 was investigated by immunoprecipitation. B. Various TRIM72 and IRS-1 mutants. C. Mid and Rear regions of IRS-1 bind with TRIM72. Myc-TRIM72 and Flag-IRS-1 mutant genes were transfected into 293 cells for 30 hours and MG132 (proteasome inhibitor) was treated for 12 hours. Interaction of TRIM72 and IRS-1 mutant proteins was investigated by immunoprecipitation. D. IRS-1 interacts with the coiled-coil domain of TRIM72. Flag-IRS-1 and Myc-TRIM72 mutant genes were transfected into 293 cells for 30 hours and MG132 (proteasome inhibitor) was treated for 12 hours. Interaction of IRS-1 and TRIM72 mutant proteins was investigated by immunoprecipitation.
Figure 9B:
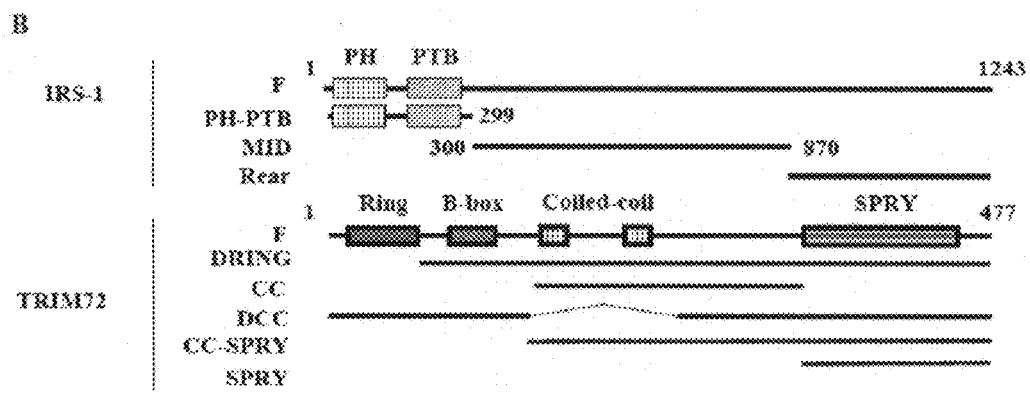
Figure 9C:
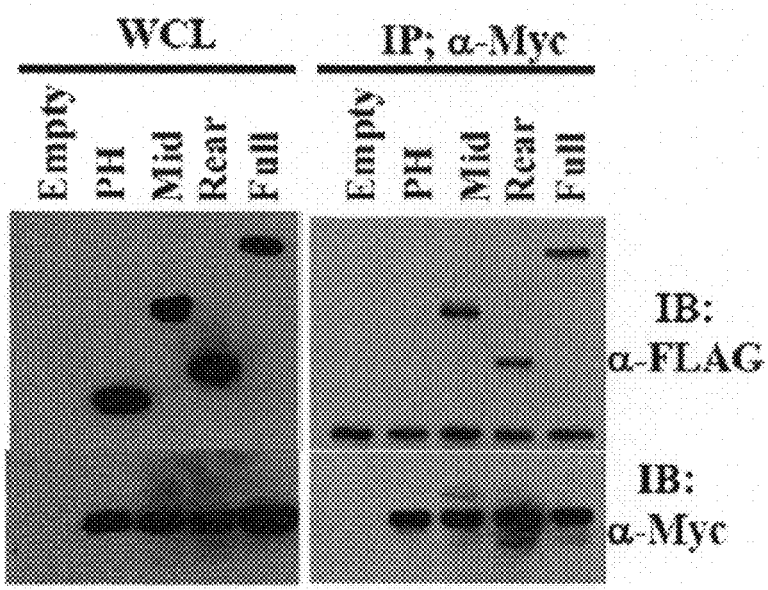
Figure 9D:
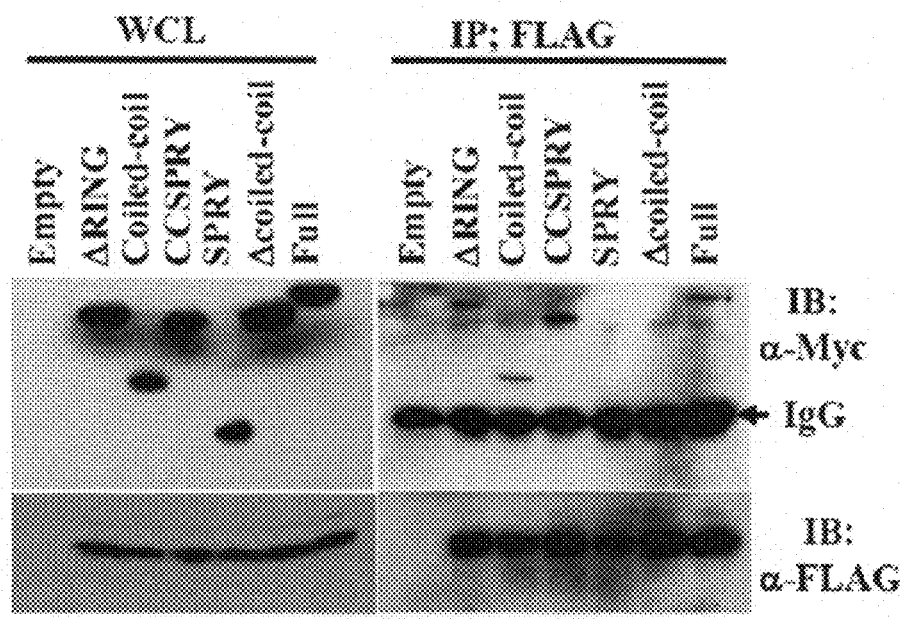

Next, the effect of TRIM72 on IGF-1-induced tyrosine phosphorylation of IGFR and IRS-1 was investigated. The tyrosine phosphorylation of IGFR induced by IGF-I was not changed by TRIM72 overexpression or knockdown (FIG. 8). However, as shown in FIG. 8, the tyrosine phosphorylation of IRS-1 was decreased by TRIM72 overexpression, but increased by TRIM72 knockdown. Moreover, the molecular association of IRS-1 with PI3K after IGF-I stimulation was weakened by TRIM72 overexpression, but fortified by TRIM72 knockdown. This result shows that TRIM72 inhibits IGF-1-induced IRS-1 activation by binding with IGFR or IRS-1. In order to demonstrate this, the molecular association of TRIM72 with IRS-1 was tested by endogenous immunoprecipitation in C2C12 myotubes treated with IGF-I for 0, 5 and 30 minutes. As shown in FIG. 9A, TRIM72 and IRS-1 were tightly associated together even in the absence of IGF-I stimulation. In order to analyze the binding domains of TRIM72 and IRS-1, various mutants of both genes were manufactured (FIG. 9B) and transfected into 293 cells. Then, the binding activity was investigated by immunoprecipitation. As shown in FIGS. 9C and 9D, the Mid (300-870) and Rear (871-1243) regions of IRS-1 bound with the coiled-coil domain of TRIM72. It should be noted that the 293 cells were treated with MG132 (proteasome inhibitor) after transferring IRS-1 and TRIM72.

Result 6: TRIM72 Mutant with no RING Domain is a Dominant Negative Form of TRIM72.

TRIM72 has a consensus sequence in the RING domain binding with $Zn^{2+}$. The $Zn^{2+}$-binding sequence has ubiquitin E3 ligase activity (FIG. 10A). Thus, DN-TRIM72 mutant genes without the RING domain (ΔRING TRIM72) or the 14th amino acid of which was substituted from cystine to alanine (C14A TRIM72) were manufactured. Wild type TRIM72, ΔRING TRIM72 and C14A TRIM72 genes were expressed in myoblasts and muscle differentiation was induced. Whereas wild type TRIM72 inhibited muscle differentiation, ΔRING TRIM72 and DN-TRIM72 enhanced muscle differentiation (FIG. 10B). It is conjectured that AIR-ING TRIM72 and C14A TRIM72 acted as dominant negative form of TRIM72.

Result 7: IRS-1 Protein is Degraded by TRIM72.

Figure 11A:
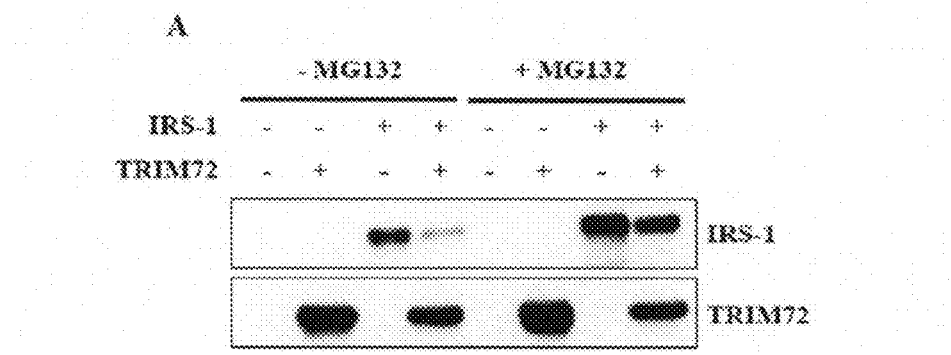
FIG. 11 shows that TRIM72 is an E3 ligase which promotes the degradation of IRS-1. A. IRS-1 (6 μg) and TRIM72 (2 μg) were transfected into HEK 293 cells for 30 hours and expression of IRS-1 and TRIM72 was investigated after treating with the proteosomal degradation inhibitor MG132 for 10 hours. B. IRS-1 (3 μg) and TRIM72 at various concentrations (0, 0.5, 1, 2 μg) were transfected into 293 cells for 30 hours and expression of IRS-1 was investigated. C. HA-TRIM72 (or HA-TRIM72 C14A), Flag-IRS-1 and His-ubiquitin were transfected into 293 cells for 30 hours and MG132 was treated for 10 hours. Ubiquitination of IRS-1 was identified by immunoblotting using His after immunoprecipitation with Flag antibody. Red brace denotes ubiquitination of IRS-1.
Figure 11B:
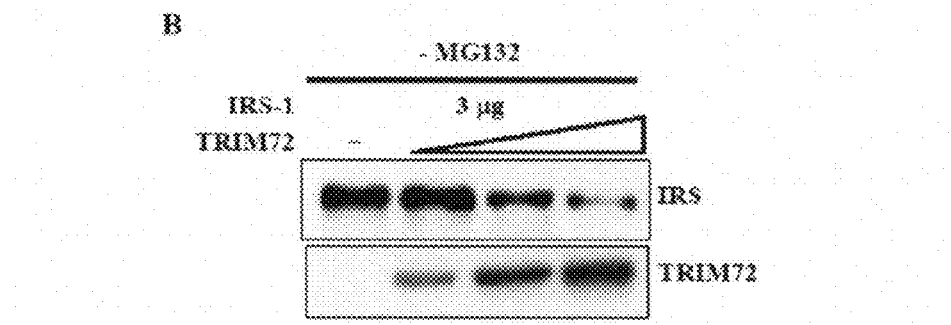
Figure 11C:
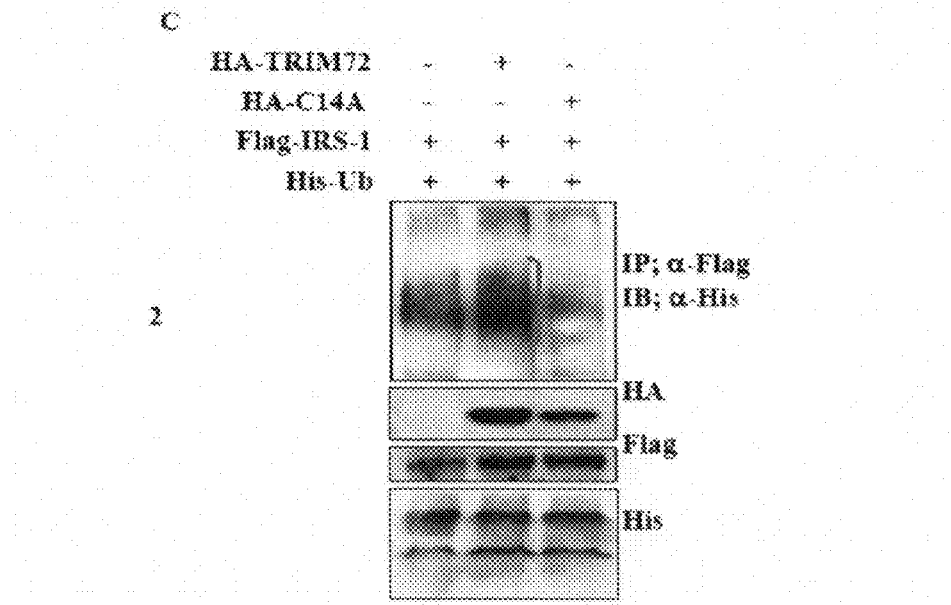

As shown in FIG. 9, treatment with MG132 (proteasome inhibitor), which degrades protein through ubiquitination, is necessary to express TRIM72 and IRS-1 genes. This indicates that TRIM72 having E3 ligase activity may target IRS-1 and promote its ubiquitination. In order to explore this possibility, it was investigated whether the expression of IRS-1 changed depending on the presence or absence of the TRIM72 gene. As shown in FIG. 11A, IRS-1 was expressed normally in the absence of TRIM72, but its expression decreased in the presence of TRIM72. Further, the expression of IRS-1 decreased as the expression of TRIM72 increased (FIG. 11B). However, when MG132 was treated, IRS-1 was expressed normally even in the presence of TRIM72. This result suggests that TRIM72 is an E3 ligase that ubiquitinates IRS-1. In order to identify whether TRIM72 actually promotes ubiquitination of IRS-1, TRIM72, IRS-1 and ubiquitin were co-expressed in 293 cells and the ubiquitination of IRS-1 was investigated. As shown from FIG. 11C, TRIM72 increased IRS-1 ubiquitination, but TRIM72 C14A completely inhibited IRS-1 ubiquitination.

Result 8: TRIM72 Promotes Ubiquitination of M-Cadherin by Interacting with M-Cadherin.

Figure 12A:
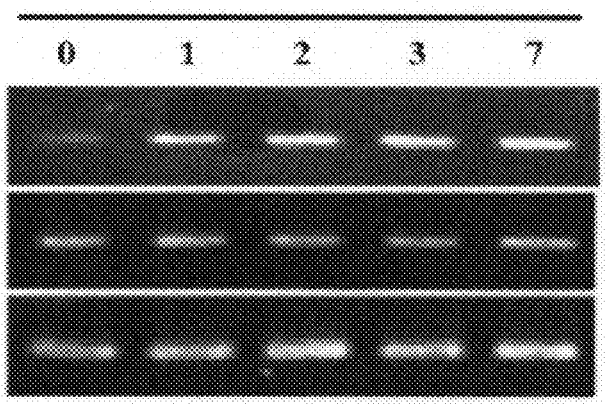
FIG. 12 shows that TRIM72 promotes ubiquitination of M-Cadherin. A-B. Change of the amount of mRNA and protein for M-Cadherin and N-Cadherin during muscle differentiation. C-D. Overexpression of TRIM72 in myoblasts results in decreased M-Cadherin. E. Inhibition of TRIM72 expression in myotubes results in increased M-Cadherin. F. Inhibition of TRIM72 expression in myotubes results in reduced ubiquitination of M-Cadherin and increased binding of M-Cadherin with δ-Catenin and p120 catenin.
Figure 12B:
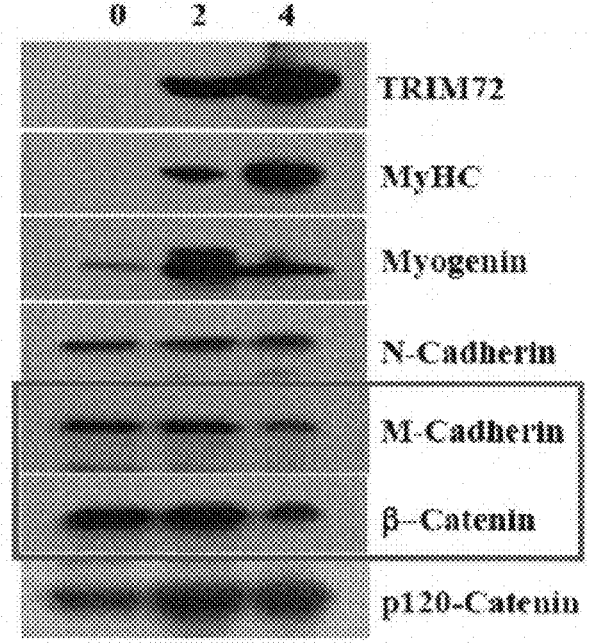
Figure 12C:
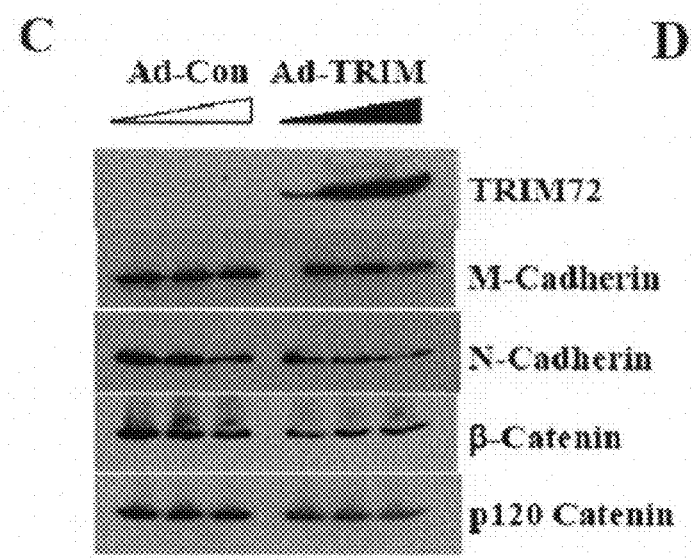
Figure 12D:
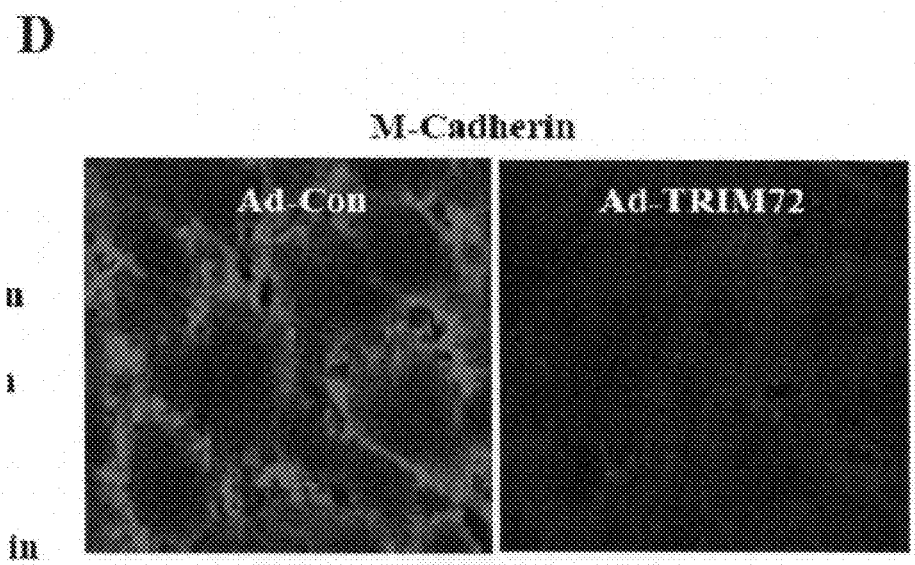
Figure 12E:
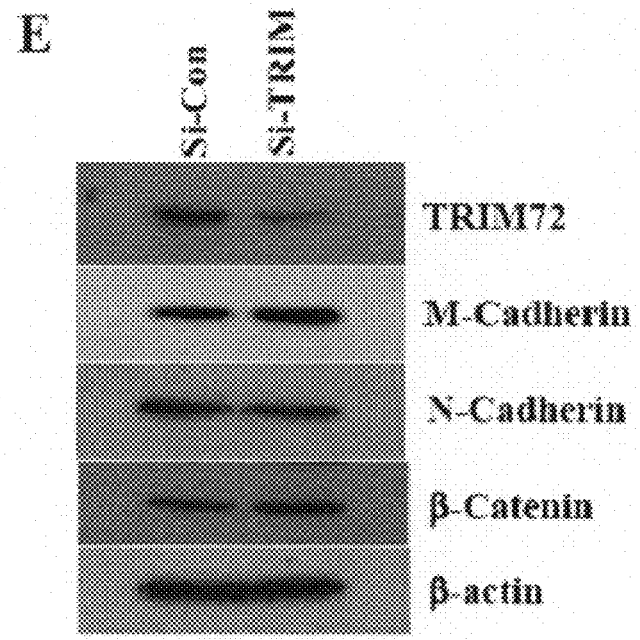
Figure 12F:
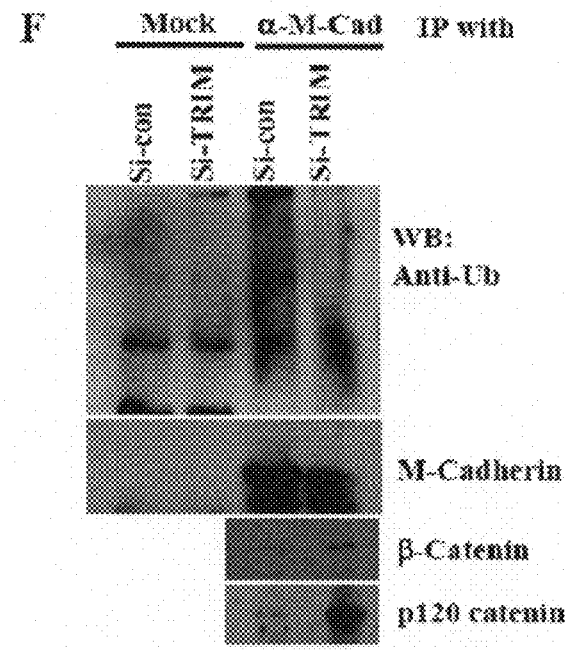

The first event necessary for differentiation of muscle cells is the fusion between myoblasts. For the myoblasts to fuse together, the cell adhesion proteins N-Cadherin and M-Cadherin are essential. Cadherins are known to induce cell cycle arrest via 13-Catenin and p120. Interestingly, TRIM72 overexpression in myoblasts completely inhibits fusion between cells (FIG. 6), suggesting that TRIM72 might be a negative regulator of N-Cadherin or M-Cadherin activity. In order to test this, the amount of mRNAs for N-Cadherin and M-Cadherin during muscle differentiation was monitored by RT-PCR. There was no change since the muscle differentiation started (FIG. 12A). However, the amount of the proteins M-Cadherin and β-Catenin began to decrease 4 days after beginning of the muscle differentiation (FIG. 12B). The fact that the amount of the protein M-Cadherin decreased while the amount of corresponding mRNA was maintained constant during muscle differentiation shows that cell fusion is regulated by degradation of proteins. Since the amount of M-Cadherin decreases during muscle differentiation by TRIM72 expression, the expression of M-Cadherin might be controlled by TRIM72. In order to test this, TRIM72 was overexpressed in myoblasts and the expression of M-Cadherin was monitored. As shown from FIGS. 12C and 12D, the expression of M-Cadherin decreased in myoblasts where TRIM72 was overexpressed. In contrast, inhibition of TRIM72 in myoblasts using Si-RNA resulted in increased expression of M-Cadherin (FIG. 12E). This result strongly suggests that TRIM72 can promote the degradation of M-Cadherin. In order to test this, ubiquitination of M-Cadherin was investigated in myotubes under reduced amount of TRIM72. As shown from FIG. 12F, Si-Control treated cells showed stained band (which denotes ubiquitination), whereas Si-TRIM72-treated cells did not. This strongly indicates that the ubiquitination of M-Cadherin is inhibited in the absence of TRIM72. Further, inhibition of TRIM72 expression by Si-RNA resulted in increase binding between M-cadherin and catenins (β-Catenin and p120 catenin).

For the TRIM72 to ubiquitinate M-Cadherin, three should be an interaction between the TRIM72 and M-Cadherin proteins. In order to test this, the cellular protein of myotubes was immunoprecipitated using TRIM72 antibody or M-Cadherin antibody, and it was investigated whether M-Cadherin or TRIM72 existed in each immunoprecipitant. As shown from FIGS. 12G and 12H, TRIM72 and M-Cadherin were strongly associated with each other. This result shows that TRIM72 binds with M-Cadherin and promotes ubiquitination of M-Cadherin, thereby reducing the amount of the M-Cadherin protein and inhibiting excessive fusion of myoblasts.

Result 9: TRIM72 Promoter Contains E-Boxes for Binding with MyoD.

Figure 13A:
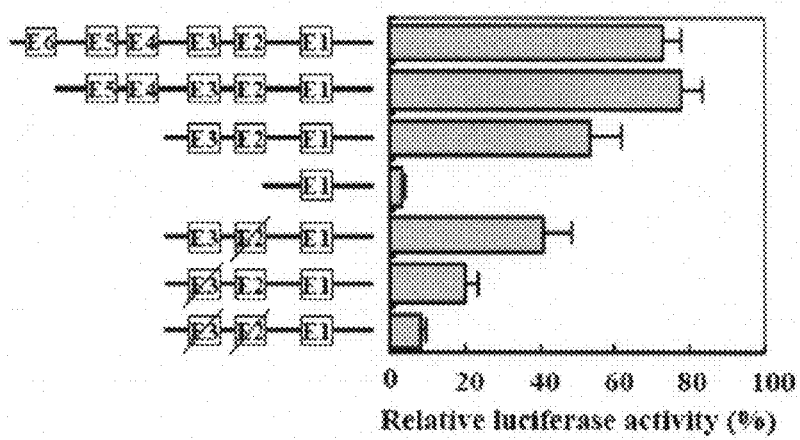
FIG. 13 shows that the TRIM72 promoter contains E-boxes for binding with MyoD. A. E2 and E3 are essential in transcription of CEMI. Various CEMI promoter mutant-luciferase fused genes were expressed in C2C12 myoblasts for 16 hours and muscle differentiation was induced for 48 hours. Luciferase activity was measured to investigate the transcription ability of the CEMI promoter mutants. B-D. MyoD is a transcription factor essential in the activation of CEMI promoter. A CEMI promoter gene having E1, E2 and E3 and MyoD, Myf5, Myogenin or Mrf4 gene were expressed in C2C12 myoblasts (B), NIH 3T3 cells (C) and 293 cells (D) for 48 hours, and then luciferase activity was measured. E. Binding of MyoD with E2 and E3 of CEMI was identified by CHIP assay. B=myoblasts; T=myotubes.
Figure 13B:
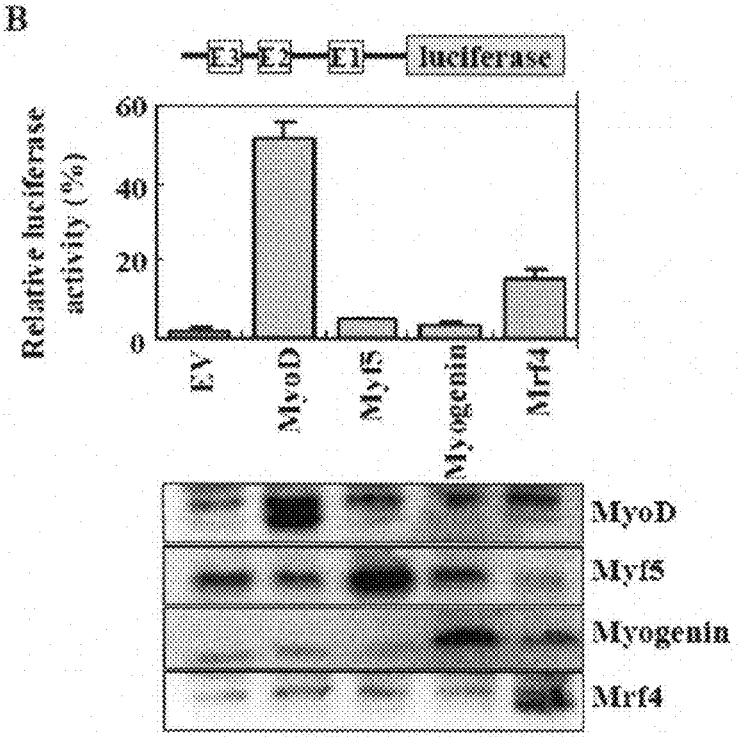
Figure 13C:
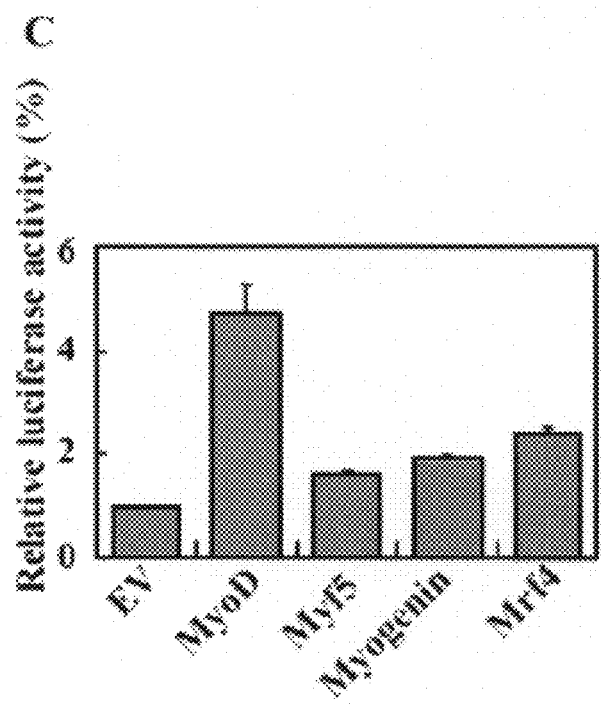
Figure 13D:
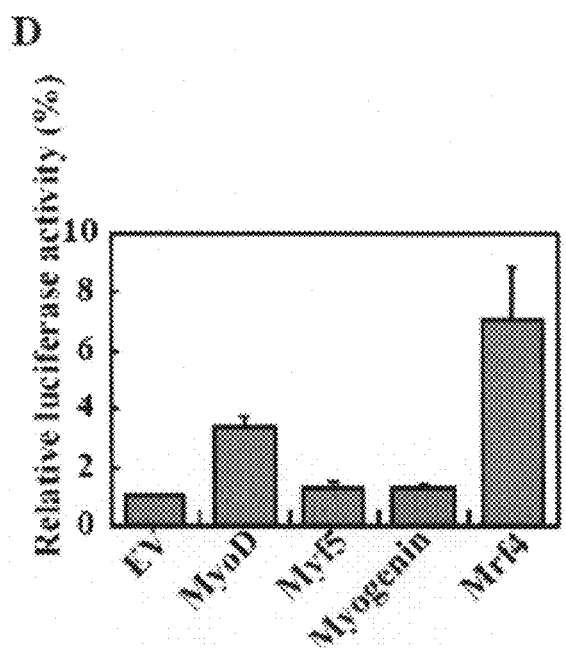
Figure 13E:
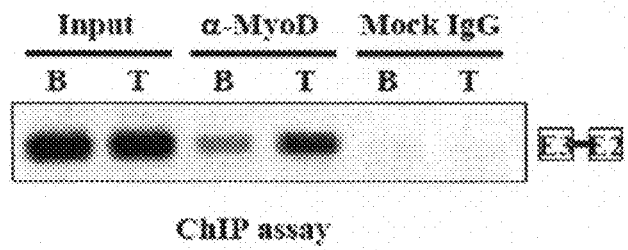

Since TRIM72 expression is gradually increased during myogenesis (FIG. 4), it is tempting to speculate that the TRIM72 promoter contains E-boxes that are binding sites for the activated MyoD. Indeed, the TRIM72 promoter contained six E-boxes (FIG. 13A). To determine the E-boxes required for MyoD-induced TRIM72 expression, the luciferase report ers with various truncation mutants in TRIM72 promoter were transfected into C2C12 myoblasts. Two days after differentiation into myotubes, luciferase activity was measured for the promoter activity. As shown from FIG. 13A, truncation or mutation of E2 and E3 boxes led to decreased TRIM72 promoter activity. Therefore, it can be seen that both E2 and E3 boxes were required for TRIM72 transcription. Further, it was shown that the TRIM72 promoter activity was significantly increased in C2C12 myoblasts, NIH3T3 cells and 293T cells by the transient expression of MyoD and Mrf4 (FIGS. 13B-D). In addition, MyoD was specifically associated with the E2 and E3 boxes of the TRIM72 promoter in myotubes, as determined by chromatin immunoprecipitation (ChIP) (FIG. 13E), indicating that MyoD activated during myogenesis is required for TRIM72 transcription.

Figure 14A:
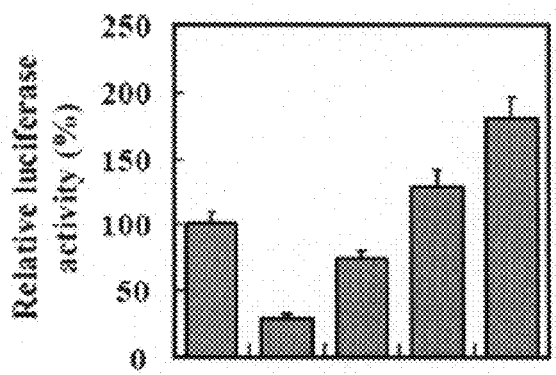
FIG. 14 shows that activation of AKT is essential for CEMI promoter activity. A. CEMI promoter-luciferase fused gene having E2 and E3 was expressed in C2C12 myoblasts for 24 hours and muscle differentiation into myotubes was induced for 24 hours. While inducing muscle differentiation, PI3K inhibitor (LY294002, 10 μM), mTOR inhibitor (rapamycin, 100 nM), GSK3β inhibitor (LiCl, 5 mM) and MAPK inhibitor (PD98059, 10 μM) were treated and luciferase activity was measured. B. CEMI promoter-luciferase fused gene having E2 and E3 and MyoD gene were expressed in C2C12 myoblasts for 24 hours. After treating with various agents for 24 hours, luciferase activity was measured. C. CEMI promoter-luciferase fused gene having E2 and E3 and constant active-(CA-)-AKT, CA-Foxo1 or CA-GSK3β were expressed in C2C12 myoblasts for 24 hours. After inducing muscle differentiation into myotubes for 24 hours, luciferase activity was measured. The panel below shows the expression amount of CA-AKT, CA-Foxo1 and CA-GSK3β identified by Western blotting. D. CEMI promoter-luciferase fused gene having E2 and E3 and SiRNA (Control-SiRNA or AKT1-SiRNA) were simultaneously treated in myoblasts for 24 hours. After inducing differentiation for 24 hours, luciferase activity was measured. The panel below shows the expression amount of AKT1 identified by Western blotting.
Figure 14B:
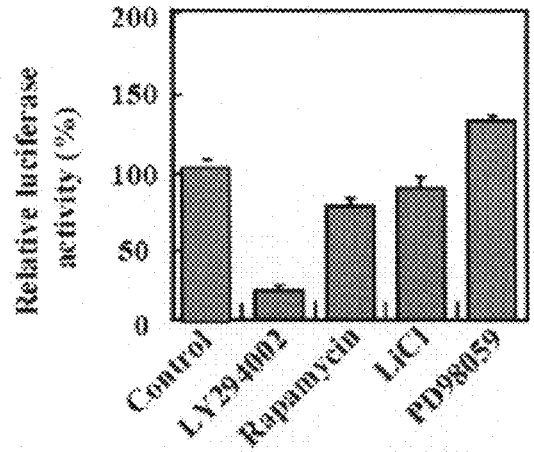
Figure 14C:
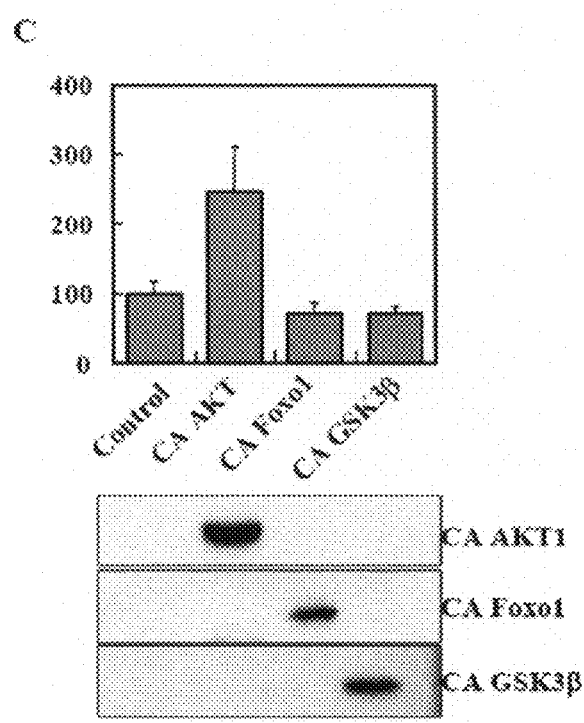
Figure 14D:
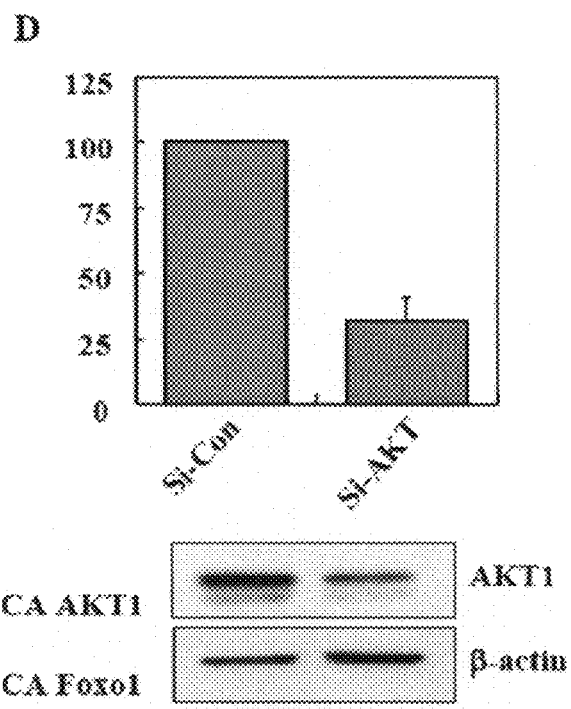

Further, the IGF signaling pathway inducing TRIM72 transcription was dissected by pharmacological approaches. As shown from FIG. 14A, TRIM72 transcription in IGF-I induced muscle differentiation decreased by 4 times when PI3K was inhibited by LY294002, whereas there was no change when mTOR was inhibited by rapamycin or when GSK313 was inhibited by LiCl. In addition, MyoD-dependent TRIM72 transcription in myoblasts was also decreased by LY292002 but was not affected by rapamycin or LiCl (FIG. 14B). The IGF signaling pathway inducing TRIM72 transcription was also analyzed by genetic approaches. The TRIM72 promoter activity was increased to 2-fold by the expression of constitutively active AKT, but not changed by that of FOXO1 or GSK313 in myotubes (FIG. 14C). In addition, the TRIM72 promoter activity was decreased in myotubes by silencing of AKT (FIG. 14D). With the pharmacological and genetic studies, it can be concluded that TRIM72 transcription requires the MyoD activated by the PI3K-AKT pathway, not depending on mTOR, FOXO and GSK313.

Result 10: TRIM72 Operation Model; TRIM72 is a Muscle Differentiation Inhibiting Protein which Targets IRS-1 and Blocks IGF-I Signaling.

Figure 15:
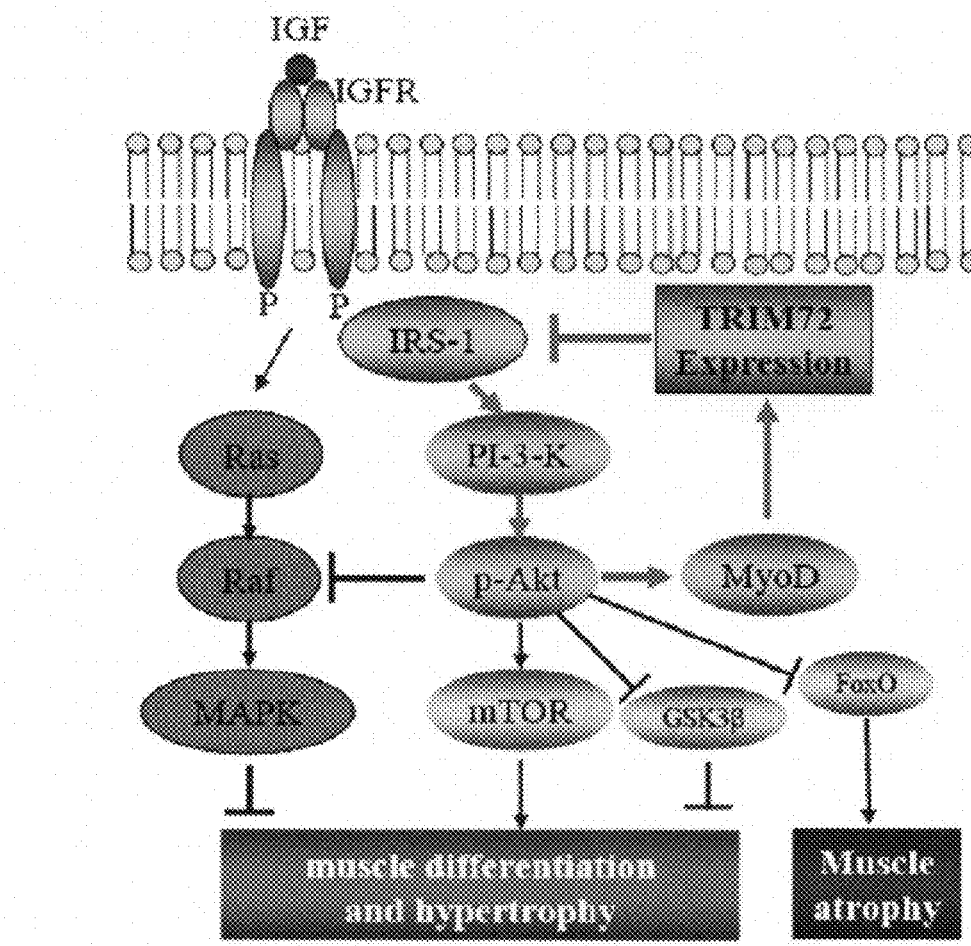
FIG. 15 schematically illustrates that TRIM72 is a negative feedback regulator inhibiting muscle differentiation or hypertrophy.

Based on these test results, the mechanism by which TRIM72 inhibits muscle differentiation can be proposed as shown in FIG. 15. As TRIM72 is expressed along with muscle differentiation (The inventors have identified that TRIM72 expression is dependent on PI3K/AKT signaling), it binds with IRS-1, thereby blocking the IGF-I-induced tyrosine phosphorylation of IRS-1 and inhibiting IGF-I signaling. This clearly shows that TRIM72 is a negative feedback regulator that controls excessive muscle enhancement or hypertrophy.

INDUSTRIAL APPLICABILITY

As described, the inventors of the present invention have identified that TRIM72 overexpression inhibits myogenesis whereas TRIM72 knockdown enhances myogenesis, and first elucidated that TRIM72 is a negative regulator of skeletal muscle differentiation. Accordingly, the inhibition of TRIM72 acts exclusively on skeletal muscle and heart muscle, but does not affect IGF-I signaling pathway in other tissues. Therefore, a drug or gene therapy using TRIM72 as a target may be helpful in treating obesity and type 2 diabetes by promoting skeletal muscle differentiation, hypertrophy and energy consumption in adipose tissue and inducing strong muscle by promoting physiological hypertrophy of heart muscle, without cancer or other side effects. Further, cattle with enhanced muscle mass may be produced by control of TRIM72 gene expression or production of TRIM72 gene-modified animals. And, candidate materials inhibiting the interaction of TRIM72 and M-Cadherin (or IRS-1) may be used as muscle enhancer or heart enhancer. In addition, the muscle enhancer or heart enhancer may be developed into treatments for obesity, type 2 diabetes, muscle disease, cardiac hypertrophy, or the like.

The invention claimed is:

1. A method for enhancing myogenesis, which comprises administering to a subject an effective dose of an expression or action inhibitor of TRIM72 protein.

2. The method for enhancing myogenesis according to claim 1, wherein the TRIM72 protein has an amino acid sequence of SEQ ID NO: 1 or 2.

3. The method for enhancing myogenesis according to claim 1, wherein the expression or action inhibitor of TRIM72 protein downregulates the transcription of the TRIM72 gene, translation of TRIM72 gene product, or inhibits the action of TRIM72 protein.

4. The method for enhancing myogenesis according to claim 1, wherein the expression inhibitor of TRIM72 protein is a TRIM72 siRNA (short interfering RNA) having a base sequence complementary to the mRNA of TRIM72 gene or a gene encoding the TRIM72siRNA.

5. The method for enhancing myogenesis according to claim 4, wherein the TRIM72 siRNA has a base sequence of SEQ ID NO: 3.

6. The method for enhancing myogenesis according to claim 1, wherein the expression or action inhibitor of TRIM72 protein enhances PI3K/AKT activation induced by IGF-1.

7. The method for enhancing myogenesis according to claim 1, wherein the expression or action inhibitor of TRIM72 protein improves the interaction of IRS-1 and PI3K by increasing tyrosine phosphorylation of IRS-1.

8. The method for enhancing myogenesis according to claim 1, wherein the expression or action inhibitor of TRIM72 protein inhibits ubiquitination of IRS-1or M-Cadherin by TRIM 72.

9. The method for enhancing myogenesis according to claim 1, wherein the expression or action inhibitor of TRIM72 protein comprises a mutant TRIM72 protein or a gene encoding the same.

10. The method for enhancing myogenesis according to claim 1, wherein myogenesis occurs in a skeletal muscle cell.

11. The method for enhancing myogenesis according to claim 1, wherein myogenesis occurs a cardiac muscle cell.

12. The method for enhancing myogenesis according to claim 1, wherein the expression or action inhibitor of TRIM72 protein promotes muscle cell differentiation.

13. The method for enhancing myogenesis according to claim 1, wherein enhancing myogenesis increases muscle mass in the subject.

14. The method for enhancing myogenesis according to claim 13, wherein the subject is a human or a non-human animal 15. The method for enhancing myogenesis according to claim 13, wherein the subject has obesity, type 2 diabetes, muscle disease, or cardiac hypertrophy.

* * * * *

SEQUENCE LISTING

```
<160> NUMBER OF SEQ ID NOS: 10

<210> SEQ ID NO 1
<211> LENGTH: 477
<212> TYPE: PRT
<213> ORGANISM: Mus musculus

<400> SEQUENCE: 1

Met Ser Ala Ala Pro Gly Leu Leu Arg Gln Glu Leu Ser Cys Pro Leu
  1               5                  10                  15

Cys Leu Gln Leu Phe Asp Ala Pro Val Thr Ala Glu Cys Gly His Ser
             20                  25                  30

Phe Cys Arg Ala Cys Leu Ile Arg Val Ala Gly Glu Pro Ala Ala Asp
         35                  40                  45

Gly Thr Val Ala Cys Pro Cys Cys Gln Ala Pro Thr Arg Pro Gln Ala
     50                  55                  60

Leu Ser Thr Asn Leu Gln Leu Ser Arg Leu Val Glu Gly Leu Ala Gln
 65                  70                  75                  80

Val Pro Gln Gly His Cys Glu Glu His Leu Asp Pro Leu Ser Ile Tyr
                 85                  90                  95

Cys Glu Gln Asp Arg Thr Leu Val Cys Gly Val Cys Ala Ser Leu Gly
            100                 105                 110

Ser His Arg Gly His Arg Leu Leu Pro Ala Ala Glu Ala Gln Ala Arg
        115                 120                 125
```

```
Leu Lys Thr Gln Leu Pro Gln Gln Lys Met Gln Leu Gln Glu Ala Cys
        130                 135                 140

Met Arg Lys Glu Lys Thr Val Ala Val Leu Glu His Gln Leu Val Glu
145                 150                 155                 160

Val Glu Glu Thr Val Arg Gln Phe Arg Gly Ala Val Gly Glu Gln Leu
                    165                 170                 175

Gly Lys Met Arg Met Phe Leu Ala Ala Leu Glu Ser Ser Leu Asp Arg
                180                 185                 190

Glu Ala Glu Arg Val Arg Gly Asp Ala Gly Val Ala Leu Arg Arg Glu
                195                 200                 205

Leu Ser Ser Leu Asn Ser Tyr Leu Glu Gln Leu Arg Gln Met Glu Lys
        210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ser Pro
                    245                 250                 255

Pro Pro Ala Arg Leu Asp Ile Gln Leu Pro Val Ile Ser Asp Asp Phe
                260                 265                 270

Lys Phe Gln Val Trp Lys Lys Met Phe Arg Ala Leu Met Pro Ala Leu
                275                 280                 285

Glu Glu Leu Thr Phe Asp Pro Ser Ser Ala His Pro Ser Leu Val Val
        290                 295                 300

Ser Ser Ser Gly Arg Arg Val Glu Cys Ser Asp Gln Lys Ala Pro Pro
305                 310                 315                 320

Ala Gly Glu Asp Thr Arg Gln Phe Asp Lys Ala Val Ala Val Val Ala
                    325                 330                 335

Gln Gln Leu Leu Ser Gln Gly Glu His Tyr Trp Glu Val Glu Val Gly
                340                 345                 350

Asp Lys Pro Arg Trp Ala Leu Gly Val Met Ala Ala Asp Ala Ser Arg
                355                 360                 365

Arg Gly Arg Leu His Ala Val Pro Ser Gln Gly Leu Trp Leu Leu Gly
        370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Pro Pro Ala Arg Ile Gly Leu Tyr
                    405                 410                 415

Leu Ser Phe Ala Asp Gly Val Leu Ala Phe Tyr Asp Ala Ser Asn Pro
                420                 425                 430

Asp Val Leu Thr Pro Ile Phe Ser Phe His Glu Arg Leu Pro Gly Pro
                435                 440                 445

Val Tyr Pro Ile Phe Asp Val Cys Trp His Asp Lys Gly Lys Asn Ala
        450                 455                 460

Gln Pro Leu Leu Leu Val Gly Pro Glu Gln Glu Gln Ala
465                 470                 475

<210> SEQ ID NO 2
<211> LENGTH: 477
<212> TYPE: PRT
<213> ORGANISM: Homo sapiens

<400> SEQUENCE: 2

Met Ser Ala Ala Pro Gly Leu Leu His Gln Glu Leu Ser Cys Pro Leu
  1               5                  10                  15

Cys Leu Gln Leu Phe Asp Ala Pro Val Thr Ala Glu Cys Gly His Ser
                20                  25                  30
```

```
Phe Cys Arg Ala Cys Leu Gly Arg Val Ala Gly Glu Pro Ala Ala Asp
         35                  40                  45

Gly Thr Val Leu Cys Pro Cys Cys Gln Ala Pro Thr Arg Pro Gln Ala
     50                  55                  60

Leu Ser Thr Asn Leu Gln Leu Ala Arg Leu Val Glu Gly Leu Ala Gln
 65                  70                  75                  80

Val Pro Gln Gly His Cys Glu His Leu Asp Pro Leu Ser Ile Tyr
                 85                  90                  95

Cys Glu Gln Asp Arg Ala Leu Val Cys Gly Val Cys Ala Ser Leu Gly
             100                 105                 110

Ser His Arg Gly His Arg Leu Leu Pro Ala Ala Glu Ala His Ala Arg
         115                 120                 125

Leu Lys Thr Gln Leu Pro Gln Gln Lys Leu Gln Leu Gln Glu Ala Cys
 130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                 165                 170                 175

Gly Lys Met Arg Val Phe Leu Ala Ala Leu Glu Gly Ser Leu Asp Cys
             180                 185                 190

Glu Ala Glu Arg Val Arg Gly Glu Ala Gly Val Ala Leu Arg Arg Glu
         195                 200                 205

Leu Gly Ser Leu Asn Ser Tyr Leu Glu Gln Leu Arg Gln Met Glu Lys
 210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                 245                 250                 255

Pro Pro Ala Arg Leu Asp Ile Gln Leu Pro Ile Ile Ser Asp Asp Phe
             260                 265                 270

Lys Phe Gln Val Trp Arg Lys Met Phe Arg Ala Leu Met Pro Ala Leu
         275                 280                 285

Glu Glu Leu Thr Phe Asp Pro Ser Ser Ala His Pro Ser Leu Val Val
 290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Ala
                 325                 330                 335

His Gln Gln Leu Ser Glu Gly Glu His Tyr Trp Glu Val Asp Val Gly
             340                 345                 350

Asp Lys Pro Arg Trp Ala Leu Gly Val Ile Ala Ala Glu Ala Pro Arg
         355                 360                 365

Arg Gly Arg Leu His Ala Val Pro Ser Gln Gly Leu Trp Leu Leu Gly
 370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                 405                 410                 415

Leu Ser Phe Gly Asp Gly Val Leu Ser Phe Tyr Asp Ala Ser Asp Ala
             420                 425                 430

Asp Ala Leu Val Pro Leu Phe Ala Phe His Glu Arg Leu Pro Arg Pro
         435                 440                 445

Val Tyr Pro Phe Phe Asp Val Cys Trp His Asp Lys Gly Lys Asn Ala
```

```
                        450                 455                 460
Gln Pro Leu Leu Leu Val Gly Pro Glu Gly Ala Glu Ala
465                 470                 475

<210> SEQ ID NO 3
<211> LENGTH: 21
<212> TYPE: RNA
<213> ORGANISM: Artificial Sequence
<220> FEATURE:
<223> OTHER INFORMATION: TRIM72 siRNA

<400> SEQUENCE: 3
uucgugcgga guucuguguc g                                                     21

<210> SEQ ID NO 4
<211> LENGTH: 417
<212> TYPE: PRT
<213> ORGANISM: Mus musculus

<400> SEQUENCE: 4

Arg Pro Gln Ala Leu Ser Thr Asn Leu Gln Leu Ser Arg Leu Val Glu
  1               5                  10                  15

Gly Leu Ala Gln Val Pro Gln Gly His Cys Glu Glu His Leu Asp Pro
             20                  25                  30

Leu Ser Ile Tyr Cys Glu Gln Asp Arg Thr Leu Val Cys Gly Val Cys
         35                  40                  45

Ala Ser Leu Gly Ser His Arg Gly His Arg Leu Leu Pro Ala Ala Glu
     50                  55                  60

Ala Gln Ala Arg Leu Lys Thr Gln Leu Pro Gln Gln Lys Met Gln Leu
 65                  70                  75                  80

Gln Glu Ala Cys Met Arg Lys Glu Lys Thr Val Ala Val Leu Glu His
                 85                  90                  95

Gln Leu Val Glu Val Glu Glu Thr Val Arg Gln Phe Arg Gly Ala Val
            100                 105                 110

Gly Glu Gln Leu Gly Lys Met Arg Met Phe Leu Ala Ala Leu Glu Ser
        115                 120                 125

Ser Leu Asp Arg Glu Ala Glu Arg Val Arg Gly Asp Ala Gly Val Ala
130                 135                 140

Leu Arg Arg Glu Leu Ser Ser Leu Asn Ser Tyr Leu Glu Gln Leu Arg
145                 150                 155                 160

Gln Met Glu Lys Val Leu Glu Glu Val Ala Asp Lys Pro Gln Thr Glu
                165                 170                 175

Phe Leu Met Lys Phe Cys Leu Val Thr Ser Arg Leu Gln Lys Ile Leu
            180                 185                 190

Ser Glu Ser Pro Pro Ala Arg Leu Asp Ile Gln Leu Pro Val Ile
        195                 200                 205

Ser Asp Asp Phe Lys Phe Gln Val Trp Lys Lys Met Phe Arg Ala Leu
    210                 215                 220

Met Pro Ala Leu Glu Glu Leu Thr Phe Asp Pro Ser Ser Ala His Pro
225                 230                 235                 240

Ser Leu Val Val Ser Ser Gly Arg Arg Val Glu Cys Ser Asp Gln
                245                 250                 255

Lys Ala Pro Pro Ala Gly Glu Asp Thr Arg Gln Phe Asp Lys Ala Val
            260                 265                 270

Ala Val Val Ala Gln Gln Leu Leu Ser Gln Gly Glu His Tyr Trp Glu
        275                 280                 285

Val Glu Val Gly Asp Lys Pro Arg Trp Ala Leu Gly Val Met Ala Ala
```

```
                290                 295                 300

Asp Ala Ser Arg Arg Gly Arg Leu His Ala Val Pro Ser Gln Gly Leu
305                 310                 315                 320

Trp Leu Leu Gly Leu Arg Asp Gly Lys Ile Leu Glu Ala His Val Glu
                325                 330                 335

Ala Lys Glu Pro Arg Ala Leu Arg Thr Pro Glu Arg Pro Ala Arg
                340                 345                 350

Ile Gly Leu Tyr Leu Ser Phe Ala Asp Gly Val Leu Ala Phe Tyr Asp
                355                 360                 365

Ala Ser Asn Pro Asp Val Leu Thr Pro Ile Phe Ser Phe His Glu Arg
370                 375                 380

Leu Pro Gly Pro Val Tyr Pro Ile Phe Asp Val Cys Trp His Asp Lys
385                 390                 395                 400

Gly Lys Asn Ala Gln Pro Leu Leu Leu Val Gly Pro Glu Gln Glu Gln
                405                 410                 415

Ala

<210> SEQ ID NO 5
<211> LENGTH: 417
<212> TYPE: PRT
<213> ORGANISM: Homo sapiens

<400> SEQUENCE: 5

Arg Pro Gln Ala Leu Ser Thr Asn Leu Gln Leu Ala Arg Leu Val Glu
1               5                   10                  15

Gly Leu Ala Gln Val Pro Gln Gly His Cys Glu Glu His Leu Asp Pro
                20                  25                  30

Leu Ser Ile Tyr Cys Glu Gln Asp Arg Ala Leu Val Cys Gly Val Cys
            35                  40                  45

Ala Ser Leu Gly Ser His Arg Gly His Arg Leu Leu Pro Ala Ala Glu
        50                  55                  60

Ala His Ala Arg Leu Lys Thr Gln Leu Pro Gln Gln Lys Leu Gln Leu
65                  70                  75                  80

Gln Glu Ala Cys Met Arg Lys Glu Lys Ser Val Ala Val Leu Glu His
                85                  90                  95

Gln Leu Val Glu Val Glu Glu Thr Val Arg Gln Phe Arg Gly Ala Val
                100                 105                 110

Gly Glu Gln Leu Gly Lys Met Arg Val Phe Leu Ala Ala Leu Glu Gly
            115                 120                 125

Ser Leu Asp Cys Glu Ala Glu Arg Val Arg Gly Glu Ala Gly Val Ala
130                 135                 140

Leu Arg Arg Glu Leu Gly Ser Leu Asn Ser Tyr Leu Glu Gln Leu Arg
145                 150                 155                 160

Gln Met Glu Lys Val Leu Glu Glu Val Ala Asp Lys Pro Gln Thr Glu
                165                 170                 175

Phe Leu Met Lys Tyr Cys Leu Val Thr Ser Arg Leu Gln Lys Ile Leu
            180                 185                 190

Ala Glu Ser Pro Pro Ala Arg Leu Asp Ile Gln Leu Pro Ile Ile
        195                 200                 205

Ser Asp Asp Phe Lys Phe Gln Val Trp Arg Lys Met Phe Arg Ala Leu
210                 215                 220

Met Pro Ala Leu Glu Glu Leu Thr Phe Asp Pro Ser Ser Ala His Pro
225                 230                 235                 240

Ser Leu Val Val Ser Ser Ser Gly Arg Arg Val Glu Cys Ser Glu Gln
                245                 250                 255
```

```
Lys Ala Pro Pro Ala Gly Glu Asp Pro Arg Gln Phe Asp Lys Ala Val
            260                 265                 270
Ala Val Val Ala His Gln Gln Leu Ser Glu Gly Glu His Tyr Trp Glu
        275                 280                 285
Val Asp Val Gly Asp Lys Pro Arg Trp Ala Leu Gly Val Ile Ala Ala
    290                 295                 300
Glu Ala Pro Arg Arg Gly Arg Leu His Ala Val Pro Ser Gln Gly Leu
305                 310                 315                 320
Trp Leu Leu Gly Leu Arg Glu Gly Lys Ile Leu Glu Ala His Val Glu
            325                 330                 335
Ala Lys Glu Pro Arg Ala Leu Arg Ser Pro Glu Arg Arg Pro Thr Arg
        340                 345                 350
Ile Gly Leu Tyr Leu Ser Phe Gly Asp Gly Val Leu Ser Phe Tyr Asp
    355                 360                 365
Ala Ser Asp Ala Asp Ala Leu Val Pro Leu Phe Ala Phe His Glu Arg
370                 375                 380
Leu Pro Arg Pro Val Tyr Pro Phe Phe Asp Val Cys Trp His Asp Lys
385                 390                 395                 400
Gly Lys Asn Ala Gln Pro Leu Leu Leu Val Gly Pro Glu Gly Ala Glu
            405                 410                 415
Ala

<210> SEQ ID NO 6
<211> LENGTH: 1269
<212> TYPE: DNA
<213> ORGANISM: Artificial Sequence
<220> FEATURE:
<223> OTHER INFORMATION: TRIM 72 promoter

<400> SEQUENCE: 6
gagctttgca atatctggga ctgcaagaat gttctagata gaggggtggc aaggacaaag      60
tcctcgaggg gccagggcgg ggggaagggt gaggtacagg tcagggcagt gaatggggcc     120
agatgggaat aaattgtagg tcataaggaa gactttgatt tttattctga ttaaaattta     180
tattaaccat cgaaagataa gctattaaga aagcctggtg cttccagcgg ggcaagctcc     240
agttctgagc tgtagactct ggtttcagtt cattcattta actacttacc attcattctc     300
caagcatttg gggggacggg gtgcattgtt tcagggccta tgctagaaaa taggggaaa     360 taccctcacc tgccttccca caggtggagt tagcaccatt agcgtaagtg gttgggaaat     420
gaataggtta accaacaatg tcaaggagga aggaagccag agtggaagtg ctgtagggag     480
aggggcagcc atgcttgccc actgattcta agctctagcc tggcctgagg aaaggactag     540
gccaggccag gatgtctcct actgactgct cacactccac atttagaaca gtttcccgaa     600
agctgtggga gggagtgggt aggacagcta aatatagttc ttgggccact gaactatctg     660
ggagggtgtc cactatatgc ctatcacctg ttgcatccac ccactgccat ctggccctga     720
atccctgccc ttgcattgag cctgctgctt gcttcttgct tgtcttggac acaactccga     780
tcaccctgct gttagacctg aacctgactg gtcctcctgg gagtcttttt tggcctaagt     840
tctcccacca gacttgtgag tcctgtgggc cttgagatat ggggaggag agggctgggt     900 atttgagaga ggtcagtggg aggtcaattg gagagggat tctagtaaat tccagaagag     960
tgaaggtcca gacctaggtc acagactgaa gcctgggcta aatcagtagc aaggagtttg    1020
tggagtgggt aaccggggct gataaatgcc tagttgggtc acatttgttt ttatctgggc    1080
tgagaatggc gatatacgtg cccactctgg gacgacacca catcctcttt accagatggt    1140
```

-continued

```
caaaaccaga ttctcttcca gtgtgggatg tgaggtagtt acaggatggg gctctgactg      1200
cggggccaca gacccagtgt aggattgagc tggaattctt gtaatgggac tcctcttccc      1260
aggctcacc                                                              1269

<210> SEQ ID NO 7
<211> LENGTH: 1144
<212> TYPE: DNA
<213> ORGANISM: Artificial Sequence
<220> FEATURE:
<223> OTHER INFORMATION: TRIM 72 promoter

<400> SEQUENCE: 7
ggaataaatt gtaggtcata aggaagactt tgattttat tctgattaaa atttatatta        60
accatcgaaa gataagctat taagaaagcc tggtgcttcc agcggggcaa gctccagttc      120
tgagctgtag actctggttt cagttcattc atttaactac ttaccattca ttctccaagc      180
atttgggggg acgggtgca ttgtttcagg gcctatgcta gaaaataggg ggaaataccc       240
tcacctgcct tcccacaggt ggagttagca ccattagcgt aagtggttgg gaaatgaata      300
ggttaaccaa caatgtcaag gaggaaggaa gccagagtgg aagtgctgta gggagagggg      360
cagccatgct tgcccactga ttctaagctc tagcctggcc tgaggaaagg actaggccag      420
gccaggatgt ctcctactga ctgctcacac tccacattta gaacagtttc cgaaagctg       480 tgggagggag tgggtaggac agctaaatat agttcttggg ccactgaact atctgggagg      540
gtgtccacta tatgcctatc acctgttgca tccacccact gccatctggc ctgaatccc       600 tgcccttgca ttgagcctgc tgcttgcttc ttgcttgtct tggacacaac tccgatcacc      660
ctgctgttag acctgaacct gactggtcct cctgggagtc ttttttggcc taagttctcc      720
caccagactt gtgagtcctg tgggccttga gatatggggg aggagagggc tgggtatttg      780
agagaggtca gtgggaggtc aattggagag gggattctag taaattccag aagagtgaag      840
gtccagacct aggtcacaga ctgaagcctg gctaaatca gtagcaagga gtttgtggag       900
tgggtaaccg gggctgataa atgcctagtt gggtcacatt tgttttatc tgggctgaga       960 atggcgatat acgtgcccac tctgggacga caccacatcc tctttaccag atggtcaaaa     1020
ccagattctc ttccagtgtg ggatgtgagg tagttacagg atggggctct gactgcgggg     1080
ccacagaccc agtgtaggat tgagctggaa ttcttgtaat gggactcctc ttcccaggct     1140
cacc                                                                  1144

<210> SEQ ID NO 8
<211> LENGTH: 883
<212> TYPE: DNA
<213> ORGANISM: Artificial Sequence
<220> FEATURE:
<223> OTHER INFORMATION: TRIM 72 promoter

<400> SEQUENCE: 8
gagttagcac cattagcgta agtggttggg aaatgaatag gttaaccaac aatgtcaagg       60
aggaaggaag ccagagtgga agtgctgtag ggagaggggc agccatgctt gcccactgat      120
tctaagctct agcctggcct gaggaaagga ctaggccagg ccaggatgtc tcctactgac      180
tgctcacact ccacatttag aacagtttcc gaaagctgt gggagggagt gggtaggaca       240
gctaaatata gttcttgggc cactgaacta tctgggaggg tgtccactat atgcctatca      300
cctgttgcat ccacccactg ccatctggcc tgaatccct gccttgcat tgagcctgct       360 gcttgcttct tgcttgtctt ggacacaact ccgatcaccc tgctgttaga cctgaacctg      420
```

```
actggtcctc ctgggagtct ttttggcct aagttctccc accagacttg tgagtcctgt      480
gggccttgag atatggggga ggagagggct gggtatttga gagaggtcag tgggaggtca      540
attggagagg ggattctagt aaattccaga agagtgaagg tccagaccta ggtcacagac      600
tgaagcctgg gctaaatcag tagcaaggag tttgtggagt gggtaaccgg ggctgataaa      660
tgcctagttg ggtcacattt gtttttatct gggctgagaa tggcgatata cgtgcccact      720
ctgggacgac accacatcct ctttaccaga tggtcaaaac cagattctct tccagtgtgg      780
gatgtgaggt agttacagga tggggctctg actgcgggc  cacagaccca gtgtaggatt      840
gagctggaat tcttgtaatg ggactcctct tcccaggctc acc                       883
```

<210> SEQ ID NO 9  
<211> LENGTH: 883  
<212> TYPE: DNA  
<213> ORGANISM: Artificial Sequence  
<220> FEATURE:  
<223> OTHER INFORMATION: E2 mutant TRIM72 promoter

<400> SEQUENCE: 9

```
gagttagcac cattagcgta agtggttggg aaatgaatag gttaaccaac aatgtcaagg       60
aggaaggaag ccagagtgga agtgctgtag ggagagggc  agccatgctt gcccactgat      120
tctaagctct agcctggcct gaggaaagga ctaggccagg ccaggatgtc tcctactgac      180
tgctcacact ccacatttag aacagtttcc cgaaagctgt gggagggagt gggtaggaca      240
gctaaatata gttcttgggc cactgaacta tctgggaggg tgtccactat atgcctatca      300
cctgttgcat ccacccactg caatcttgcc ctgaatccct gcccttgcat tgagcctgct      360
gcttgcttct tgcttgtctt ggacacaact ccgatcaccc tgctgttaga cctgaacctg      420
actggtcctc ctgggagtct ttttggcct aagttctccc accagacttg tgagtcctgt      480
gggccttgag atatggggga ggagagggct gggtatttga gagaggtcag tgggaggtca      540
attggagagg ggattctagt aaattccaga agagtgaagg tccagaccta ggtcacagac      600
tgaagcctgg gctaaatcag tagcaaggag tttgtggagt gggtaaccgg ggctgataaa      660
tgcctagttg ggtcacattt gtttttatct gggctgagaa tggcgatata cgtgcccact      720
ctgggacgac accacatcct ctttaccaga tggtcaaaac cagattctct tccagtgtgg      780
gatgtgaggt agttacagga tggggctctg actgcgggc  cacagaccca gtgtaggatt      840
gagctggaat tcttgtaatg ggactcctct tcccaggctc acc                       883
```

<210> SEQ ID NO 10  
<211> LENGTH: 883  
<212> TYPE: DNA  
<213> ORGANISM: Artificial Sequence  
<220> FEATURE:  
<223> OTHER INFORMATION: E3 mutant TRIM72 promoter

<400> SEQUENCE: 10

```
gagttagcac cattagcgta agtggttggg aaatgaatag gttaaccaac aatgtcaagg       60
aggaaggaag ccagagtgga agtgctgtag ggagagggc  agccatgctt gcccactgat      120
tctaagctct agcctggcct gaggaaagga ctaggccagg ccaggatgtc tcctactgac      180
tgctcacact ccacatttag aacagtttcc cgaaagctgt gggagggagt gggtaggaca      240
gctaaatata gttcttgggc cactgaacta tctgggaggg tgtccactat atgcctataa      300 cctttttgcat ccacccactg ccatctggcc ctgaatccct gcccttgcat tgagcctgct     360
gcttgcttct tgcttgtctt ggacacaact ccgatcaccc tgctgttaga cctgaacctg      420
```

```
actggtcctc ctgggagtct tttttggcct aagttctccc accagacttg tgagtcctgt        480
gggccttgag atatggggga ggagagggct gggtatttga gagaggtcag tgggaggtca        540
attggagagg ggattctagt aaattccaga agagtgaagg tccagaccta ggtcacagac        600
tgaagcctgg gctaaatcag tagcaaggag tttgtggagt gggtaaccgg ggctgataaa        660
tgcctagttg ggtcacattt gtttttatct gggctgagaa tggcgatata cgtgcccact        720
ctgggacgac accacatcct ctttaccaga tggtcaaaac cagattctct tccagtgtgg        780
gatgtgaggt agttacagga tggggctctg actgcgggggc cacagaccca gtgtaggatt       840
gagctggaat tcttgtaatg ggactcctct tcccaggctc acc                         883
```